(12) United States Patent
Austen et al.

(10) Patent No.: US 9,029,323 B2
(45) Date of Patent: May 12, 2015

(54) NEURTURIN CONJUGATES FOR PHARMACEUTICAL USE

(75) Inventors: Matthias Austen, Goettingen (DE); Marcus Geese, Goettingen (DE); Rainer Mussmann, Magden (CH); Friedrich Harder, Lindau (DE); Thomas Siegmund, Landolfshausen (DE); Martin Schneider, Goettingen (DE)

(73) Assignee: Evotec International GmbH, Hamburg (DE)

(*) Notice: Subject to any disclaimer, the term of this patent is extended or adjusted under 35 U.S.C. 154(b) by 324 days.

(21) Appl. No.: 12/774,235

(22) Filed: May 5, 2010

(65) Prior Publication Data
US 2011/0003741 A1    Jan. 6, 2011

Related U.S. Application Data

(63) Continuation-in-part of application No. PCT/EP2008/009320, filed on Nov. 5, 2008.

(30) Foreign Application Priority Data

Nov. 5, 2007  (EP) .................................... 07021493

(51) Int. Cl.
*A61K 38/18* (2006.01)
*C07K 14/475* (2006.01)
*A61K 47/48* (2006.01)

(52) U.S. Cl.
CPC .......... *C07K 14/4756* (2013.01); *A61K 38/185* (2013.01); *A61K 47/48215* (2013.01)

(58) Field of Classification Search
CPC .......................... A61K 38/185; C07K 14/475
See application file for complete search history.

(56) References Cited

U.S. PATENT DOCUMENTS

| | | |
|---|---|---|
| 2004/0265972 A1 | 12/2004 | Weintraub et al. |
| 2005/0222070 A1 | 10/2005 | Dohrmann et al. |
| 2008/0241106 A1 | 10/2008 | Austen et al. |
| 2009/0258829 A1 | 10/2009 | Harder et al. |
| 2011/0256113 A1 | 10/2011 | Austen et al. |
| 2011/0277045 A1 | 11/2011 | Dohrmann et al. |

FOREIGN PATENT DOCUMENTS

| | | |
|---|---|---|
| EP | 1872790 A | 1/2008 |
| WO | WO 97/08196 A1 | 8/1996 |
| WO | 9906064 A | 2/1999 |
| WO | WO 03/099318 A2 | 12/2003 |
| WO | 2004069176 A | 8/2004 |
| WO | WO 2005/039643 A2 | 5/2005 |
| WO | 2005051415 A | 6/2005 |
| WO | WO 2008/000447 A1 | 3/2008 |

OTHER PUBLICATIONS

Rudinger in "Peptide Hormones" (ed. J.A.Parsons) University Park Press, Baltimore, pp. 1-7 (1976).*
Pasut et al, "Protein, Peptide and Non-Peptide Drug Pegylation for Therapeutic Application", Expert Opinion on Therapeutic Patents, Informa Healthcare, vol. 14, No. 6, Jan. 1, 2004, pp. 859-894.
Caliceti et al, "Pharmacokinetic and Biodistribution Properties of Poly(ethylene glycol)—Protein Conjugates", Advanced Drug Delivery Reviews, vol. 55, Jan. 1, 2003, pp. 1261-1277.
Bowie et al., "Deciphering the Message in Protein Sequences: Tolerance to Amino Acid Substitutions," Science, vol. 247:1306-1310 (1990).
Kim et al., "Pancreas Development in the Chick Embryo," Cold Spring Harbor Symposia on Quantitative Biology, vol. 62:377-383 (1997).
Staffers et al., "Early-onset type-II diabetes mellitus (MODY4) linked to IPF1," vol. 17(2):138-139 (1997).
Wells, James A., "Additivity of Mutational Effects in Proteins," Biochemistry, vol. 29(37):8509-8517 (1990).
Baloh et al., "Functional Mapping of Receptor Specificity Domains of Glial Cell Line-derived Neurotrophic Factor (GDNF) Family Ligands and Production of GFRα1 RET-specific Agonists*," The Journal of Biological Chemistry, vol. 275(5): 3412-3420 (2000).
Greenwald et al., "Effective drug delivery by PEGylated drug conjugates," Advanced Drug Delivery Reviews, vol. 55: 217-250 (2003).
Greenwald, R.B., "PEG drugs: an overview," Journal of Controlled Release: vol. 74: 159-171 (2001).
Alfano et al., "The major determinant of the heparin binding of glial cell-line-derived neurotrophic factor is near the N-terminus and is dispensable for receptor binding," Biochem. J.; vol. 404: 131-140 (2007).

* cited by examiner

*Primary Examiner* — Robert C Hayes
(74) *Attorney, Agent, or Firm* — Ropes & Gray LLP

(57) ABSTRACT

The present invention relates to neurturin protein products conjugated to polyols and to pharmaceutical compositions comprising neurturin conjugates as active ingredients, preferably PEGylated neurturin conjugates or variants thereof, having increased bioavailability.

39 Claims, 13 Drawing Sheets

Figure 3

MQRWKAAALA   SVLCSSVLSI   WMCREGLLLS   HRLGPALVPL   HRLPRTLDAR
IARLAQYRAL   LQGAPDAMEL   RELTPWAGRP   PGPRRRAGPR   RRRARARLGA
RPCGLRELEV   RVSELGLGYA   SDETVLFRYC   AGACEAAARV   YDLGLRRLRQ
RRRLRRERVR AQPCCRPTAY EDEVSFLDAH SRYHTVHELS ARECACV ← SEQ. ID. NO. 1

Figure 4
Figure 4A
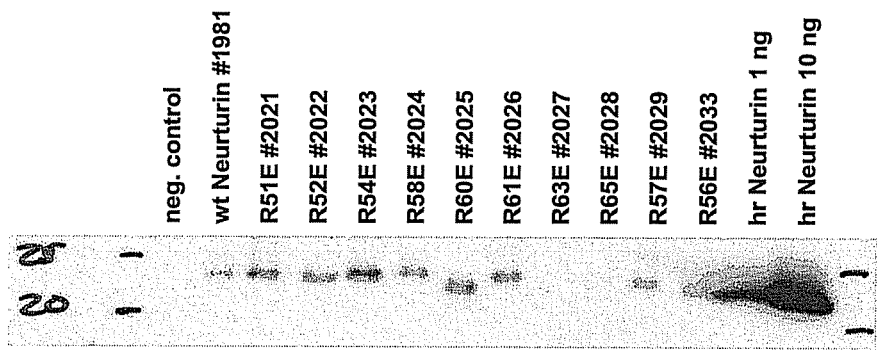
Figure 4B
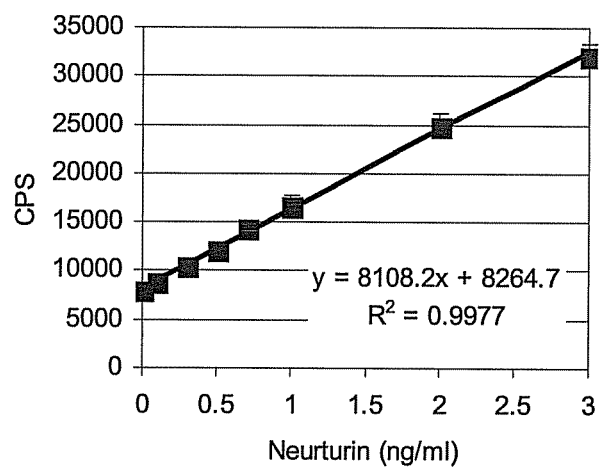

| | w/o FCS | 1% FCS | 3% FCS | 10% FCS |
|---|---|---|---|---|
| EC50 | 1.657 | 0.8837 | 0.6959 | 0.6994 |

| position of mutated amino acid (human mature Neurturin) | Neurturin Concentration [ng/ml] by Neurturin ELISA | $EC_{50}$ [ng/ml] of Neurturin activity by cellular tyrosine hydroxylase reporter gene assay |
|---|---|---|
| control | n.d. | n.d. |
| wt | 1500 | 0.71 |
| R51E | 1600 | 0.58 |
| R52E | 1500 | 0.32 |
| R54E | 1700 | 0.41 |
| R56E | 1600 | 0.48 |
| R57E | 1300 | 0.58 |
| R58E | 1200 | 0.89 |
| R60E | 1600 | 0.47 |
| R61E | 1600 | 0.48 |
| R63E | n.d. | n.d. |
| R65E | 1500 | 0.37 |
| wt (E.coli) | 1500 | 2.20 |

Figure 6

| | | |
|---|---|---|
| *Homo sapiens* (NP_004549) | DLGLRRLRQRRRLRRERVRAQPC | SEQ. ID. NO. 8 |
| *Macaca mulatta* (XP_001085705.1) | DLGLRRLRQRRRLRRERVRAQPC | SEQ. ID. NO. 9 |
| *Bos taurus* (XP_603915.2) | DLGLRRLRQRRRVRRERVRAQPC | SEQ. ID. NO. 10 |
| *Canis familiaris* (XP_854570) | DLGLRRLRQRRRVRRERVRAQPC | SEQ. ID. NO. 11 |
| *Mus musculus* (NP_032764.1) | DLGLRRLRQRRRVRRERARAHPC | SEQ. ID. NO. 12 |
| *Rattus norvegicus* (NP_445851.1) | DLGLRRLRQRRRVRKERVRAHPC | SEQ. ID. NO. 13 |
| *Ornithorhynchus anatinus* (XP_001509015.1) | DLGLRRLRQRRRVRKEKVRAQPC | SEQ. ID. NO. 14 |
| *Monodelphis domestica* (XP_001369475.1) | DLGLRRLRQRRRVRKEKIRARPC | SEQ. ID. NO. 15 |
| *Gallus gallus* (NP_001074973.1) | DLSLKSVRSRKKIRKEKVRARPC | SEQ. ID. NO. 16 |

Figure 7A

```
                        PacI    KpnI  HindIII  NcoI
      GAGCGGAAGGCCCATGAGGCCAGTTAATTAAGAGGTACCAAGCTTGCCACCATGGGCACC  SEQ.ID.NO.17
  1   ----------+---------+---------+---------+---------+---------+
      CTCGCCTTCCGGGTACTCCGGTCAATTAATTCTCCATGGTTCGAACGGTGGTACCCGTGG  SEQ.ID.NO.18
                                                       M  G  T     SEQ.ID.NO.19

BapMI                                            KasI
          PacI                                           NarI
      CCACACCTGCAGGGCTTTCTGCTGCTGTTCCCCCTGCTGCTGCGGCTGCACGGCGCCTCT
 61   ----------+---------+---------+---------+---------+---------+
      GGTGTGGACGTCCCGAAAGACGACGACAAGGGGGACGACGACGCCGACGTGCCGCGGAGA
       P  H  L  Q  G  F  L  L  L  F  P  L  L  L  R  L  H  G  A  S

GCCGGCTCTGGCGGCGGACACCACCACCATCACCACGGCGGAGGGATCGAGGGCAGAGCC
121   ----------+---------+---------+---------+---------+---------+
      CGGCCGAGACCGCCGCCTGTGGTGGTGGTAGTGGTGCCGCCTCCCTAGCTCCCGTCTCGG
       A  G  S  G  G  G  H  H  H  H  H  H  G  G  G  I  E  G  R  A

KasI
         NarI                                                BstNI
      AGACTGGGCGCCAGACCCTGCGGCCTGCGGGAGCTGGAAGTGCGGGTGTCCGAGCTGGGC
181   ----------+---------+---------+---------+---------+---------+
      TCTGACCCGCGGTCTGGGACGCCGGACGCCCTCGACCTTCACGCCCACAGGCTCGACCCG
       R  L  G  A  R  P  C  G  L  R  E  L  E  V  R  V  S  E  L  G

KasI
                                                     NarI
      CTGGGCTACGCCAGCGACGAGACAGTGCTGTTCCGGTACTGCGCTGGCGCCTGCGAGGCC
241   ----------+---------+---------+---------+---------+---------+
      GACCCGATGCGGTCGCTGCTCTGTCACGACAAGGCCATGACGCGACCGCGGACGCTCCGG
       L  G  Y  A  S  D  E  T  V  L  F  R  Y  C  A  G  A  C  E  A
```

Figure 7B

```
        XmaI
        SmaI          BstNI
      GCTGCCCGGGTGTACGACCTGGGGCTCCGGAGACTGAGACAGCGGCGGAGACTGAGGCGG
301   ----------+----------+----------+----------+----------+---------+
      CGACGGGCCCACATGCTGGACCCCGAGGCCTCTGACTCTGTCGCCGCCTCTGACTCCGCC
      A  A  R  V  Y  D  L  G  L  R  R  L  R  Q  R  R  R  L  R  R

BssHII          PstI                              BstNI
      GAGAGAGTGCGCGCCCAGCCCTGCTGCAGACCCACCGCCTACGAGGACGAGGTGTCCTTC
361   ----------+----------+----------+----------+----------+---------+
      CTCTCTCACGCGCGGGTCGGGACGACGTCTGGGTGGCGGATGCTCCTGCTCCACAGGAAG
      E  R  V  R  A  Q  P  C  C  R  P  T  A  Y  E  D  E  V  S  F

CTGGACGCCCACAGCAGATACCACACCGTGCACGAGCTGTCCGCCAGAGAATGCGCCTGC
421   ----------+----------+----------+----------+----------+---------+
      GACCTGCGGGTGTCGTCTATGGTGTGGCACGTGCTCGACAGGCGGTCTCTTACGCGGACG
      L  D  A  H  S  R  Y  H  T  V  H  E  L  S  A  R  E  C  A  C

XhoI
          HinfI         AscI
            SacI   BssHII StuI
      GTGTGATGACTCGAGCTCATGGCGCGCCTAGGCCTTGACGGCCTTCCGCCA
481   ----------+----------+----------+----------+----------+-
      CACACTACTGAGCTCGAGTACCGCGCGGATCCGGAACTGCCGGAAGGCGGT
      V  +  +
```

NEURTURIN CONJUGATES FOR PHARMACEUTICAL USE

CROSS REFERENCE TO RELATED APPLICATIONS

This application is a continuation-in-part of PCT/EP2008/009320 filed Nov. 5, 2008, which claims the benefit of European Patent Application No. 07021493.7 filed on Nov. 5, 2007, the disclosures of which are incorporated herein in their entirety by reference.

FIELD OF THE INVENTION

The present invention relates to the modification of human neurturin to increase its serum half life and pharmacokinetic profile. In particular, the invention relates to novel neurturin conjugates comprising neurturin or biologically active fragments thereof covalently attached to polyol moieties, preferably polyethylene glycol. The invention further relates to pharmaceutical compositions with increased bioavailability comprising novel neurturin conjugates as active agent for therapy, treatment, prevention and/or diagnosis of diabetes and neurodegeneration.

BACKGROUND

Pancreatic beta-cells secrete insulin in response to elevated blood glucose levels. Insulin amongst other hormones plays a key role in the regulation of the fuel metabolism. Insulin leads to the storage of glycogen and triglycerides and to the synthesis of proteins. The entry of glucose into muscles and adipose cells is stimulated by insulin. In patients who suffer from diabetes mellitus type I or LADA (latent autoimmue diabetes in adults, Pozzilli & Di Mario, 2001, Diabetes Care. 8:1460-1467) beta-cells are being destroyed due to autoimmune attack. The amount of insulin produced by the remaining pancreatic islet cells is too low, resulting in elevated blood glucose levels (hyperglycemia). In diabetes mellitus type II liver and muscle cells loose their ability to respond to normal blood insulin levels (insulin resistance). High blood glucose levels (and also high blood lipid levels) in turn lead to an impairment of beta-cell function and to an increase in beta-cell death. Interestingly, beta-cell regenerative processes like neogenesis and replication do not appear to compensate for the loss of beta cell mass in type II diabetics, thus causing a reduction in total beta-cell mass over time. Eventually the application of exogenous insulin becomes necessary in type II diabetics for an adequate control of blood glucose levels.

In type I diabetics, where beta-cells are being destroyed by autoimmune attack, treatments have been devised which modulate the immune system and may be able to stop or strongly reduce islet destruction (Raz et al., 2001, Lancet 358: 1749-1753; Chatenoud et al., 2003, Nat Rev Immunol. 3: 123-132; Homann et al., Immunity. 2002, 3:403-415). However, due to the relatively slow regeneration of human beta-cells such treatments can be more successful if they are combined with treatments that can stimulate beta-cell regeneration.

Diabetes is a very disabling disease, because today's common anti-diabetic drugs do not control blood sugar levels well enough to completely prevent the occurrence of high and low blood sugar levels. Frequently elevated blood sugar levels are toxic and cause long-term complications like for example nephropathy, retinopathy, neuropathy and peripheral vascular disease. Extensive loss of beta cells also leads to deregulation of glucagon secretion from pancreatic alpha cells which contributes to an increased risk of dangerous hypoglycemic episodes. There is also a host of related conditions, such as obesity, hypertension, heart disease and hyperlipidemia, for which persons with diabetes are substantially at risk.

Apart from the impaired quality of life for the patients, the treatment of diabetes and its long term complications presents an enormous financial burden to our healthcare systems with rising tendency. Thus, for the treatment of diabetes mellitus type I and LADA, but also for the treatment of late stages of diabetes mellitus type II there is a strong need in the art to identify factors that induce regeneration of pancreatic insulin producing beta-cells. These factors could restore normal function of the endocrine pancreas once its function is impaired or event could prevent the development or progression of diabetes type I, LADA or diabetes type II.

Neurturin is a secreted protein which is expressed in embryonic pancreas. Recombinant neurturin has been shown to stimulate the differentiation of mouse embryonic stemcells into insulin producing cells. Moreover, transgenic mice with elevated neurturin levels in the pancreas have a substantially increased pancreatic beta-cell mass. Based on these findings, the use of neurturin for the treatment of pancreatic disorders such as diabetes has been proposed (see for example WO 03/99318 and WO 2005/051415, the disclosure of which is herein incorporated by reference).

Neurturin is a member of the GDNF family of ligands (GFL) comprised of Glial cell line-derived neurotrophic factor (GDNF), Neurturin, Artemin and Persephin. Mature neurturin is a homodimer with a size of 23.6 kDa comprised of 102 amino acid monomers. Each monomer contains 3 intrachain disulfide bonds forming a cystine knot. An additional disulfide bridge is connecting the monomers.

Neurturin had previously been proposed as a treatment for neurodegenerative diseases such as Parkinsons, Alzheimers and Huntington's disease, motor neuron disorders, spinal cord injuries or hearing disorders (WO 97/08196, WO 99/06064; Akerud et al. J Neurochem. 1999; 73(1):70-78; Koeberle & Ball Neuroscience. 2002; 110(3):555-567; Bilak et al. Mol Cell Neurosci. 1999; 13(5):326-336; Perez-Navarro et al. Neuroscience. 2000; 98(1):89-96; Rosenblad et al, Eur J Neurosci. 1999; 11(5):1554-1566, the disclosures of which are herein incorporated by reference).

It was found, however, that upon convection-enhanced delivery (CED) into rat brains, the distribution volume of neurturin and the related factor GDNF was limited (Hamilton et al., Exp Neurol. 2001; 168(1):155-161). Proteins must typically be administered by injection. After injection most proteins are cleared rapidly from the body, necessitating frequent injections. In our own studies, we found that the bioavailability after subcutaneous and intravenous injection of neurturin in mammals is low. Only about 10 percent of subcutaneously injected neurturin enter the circulation. Consequently, it is difficult to achieve therapeutically useful blood levels of the proteins in patients.

Thus, there is a strong need to develop a neurturin variant with enhanced availability in patients and therewith the development of methods to prolong the circulating half-lives of protein therapeutics in the body—the bioavailability—so that neurturin as active agent does not have to be injected frequently in order to satisfy the needs of patients for "user-friendly" protein therapeutics.

Thus, the underlying problem of the present invention was to provide new variants and formulations of neurturin that enhance its bioavailability.

The problem is solved by providing the embodiments characterized in the claims.

SUMMARY OF THE INVENTION

The present invention relates to a novel neurturin conjugate comprising a polyol moiety covalently bound to a human neurturin protein product.

The present invention further relates to a pharmaceutical composition comprising at least one neurturin protein product and/or a biologically active fragment thereof which is conjugated to at least one polyethylene glycol molecule as an active ingredient together with a pharmaceutically acceptable carrier, diluent and/or adjuvant.

In a further embodiment, the present invention relates to a method for administering a pharmaceutical composition to a subject in need thereof comprising a pharmaceutically active amount of at least one modified neurturin protein product or a biologically active fragment thereof which is conjugated to at least one polyethylene glycol molecule as an active ingredient together with a pharmaceutically acceptable carrier, diluent and/or adjuvant.

It is a further aspect of the present invention to provide a method for administering a pharmaceutical composition to a subject in need thereof comprising a pharmaceutically active amount of at least one modified neurturin protein product or a biologically active fragment thereof which is conjugated to at least one polyethylene glycol molecule as an active ingredient together with a low-molecular weight substance together with a pharmaceutically acceptable carrier, diluent and/or adjuvant.

The compositions of the present invention are suitable for preventing or treating pancreatic disorders or neurodegenerative diseases, particularly pancreatic autoimmune disorders, e.g. autoimmune diabetes such as type I diabetes or LADA but also type II diabetes.

BRIEF DESCRIPTION OF THE DRAWINGS

The reporter cell line was subjected to increasing concentrations of neurturin or neurturin conjugated with PEG (PEGylated neurturin). The resulting reporter gene activity (relative light units (RLU) given on the y-axis) was plotted against the final concentration of the test agent (given on the x-axis in ng/ml; FIGS. 1A and B). Two independently produced batches of unmodified neurturin were used as experimental controls (PeproTech; Lot0805112 and Lot0106112) and their relative activity was compared to those of the three PEGylated conjugates (mono-mPEG-NHS-neurturin, mono-mPEG-CHO-neurturin and mono-CES0310-neurturin). Given values are means of at least 3 wells±S.D. The calculated $EC_{50}$ of the various tests are: Neurturin (Lot0805112, unmodified protein): $EC_{50}$=2.2 ng/ml, neurturin (Lot0106112, unmodified protein): $EC_{50}$=1.2 ng/ml, mono-CES0310-neurturin: $EC_{50}$=12 ng/ml (FIG. 1A), and neurturin (Lot0106112, unmodified protein): $EC_{50}$=3.8 ng/ml, mono-mPEG-NHS-neurturin: $EC_{50}$=9.7 ng/ml, and mono-mPEG-CHO-neurturin: $EC_{50}$=7.4 ng/ml (FIG. 1B).

FIGS. 2A and 2B show the neurturin plasma concentrations in ng/ml at various time points after the administration of 0.050 mg/kg BW (FIG. 2A) or 0.50 mg/kg BW (FIG. 2B) of neurturin or PEGylated neurturin to mice. Resulting plasma levels were determined by a neurturin ELISA assay. Time point zero shows the average background signal for neurturin in mouse serum using this ELISA assay. The background values were calculated from independently measured values from sera of 12 (FIG. 2A) or from 11 (FIG. 2B) untreated mice The other indicated values are means of measured serum levels from three animals±SD. FIG. 2A shows PK data for the neurturin conjugate mono-NHS-neurturin stemming from two independent experiments (mono-NHS-neurturin_Exp.1 and -_Exp.2). FIG. 2B shows data derived from yet another experiment where mice were treated with 0.50 mg/kg BW mono-NHS-neurturin. For area under the curve (AUC) analysis covering all measured time points, the baseline was set to 0.6 ng/ml (the average background value at the time point 0): Neurturin unmodified protein: 18.8 ng*min/ml, mono-mPEG-NHS-neurturin_Exp1: 409ng*min/ml, mono-mPEG-NHS-neurturin_Exp2: 918 ng*min/ml, mono-CES0310-neurturin: $EC_{50}$=142 ng*min/ml (FIG. 2A), and neurturin unmodified protein: 324 ng*min/ml, mono-mPEG-NHS-neurturin: 1157 ng*min/ml, and mono-mPEG-CHO-neurturin: 845 ng*min/ml (FIG. 2B). For the area under the curve (AUC) analysis (FIGS. 2A and B) of neurturin serum levels the baseline was set to 0.6 ng/ml neurturin which corresponds to the average background level determined in the serum of untreated mice.

FIG. 3:

Protein sequence of human neurturin precursor (SEQ ID NO: 1) as published by the National Center for Biotechnology Information (NCBI) (accession number: NP_004549). The sequence of the mature protein (SEQ ID NO: 5) which corresponds to the biologically as well as pharmacologically active form is highlighted in bold.

FIGS. 4A and 4B:

FIG. 4A. Expression of human neurturin and mutated neurturin variants. Native-PAGE/Western-blot of concentrated supernatant from HEK-293 cells expressing neurturin and neurturin variants (numbering of the positions according to the sequence of mature human neurturin, R: arginine, E: glutamic acid). FIG. 4B. Neurturin ELISA: Representative standard curve using human recombinant neurturin expressed from *E. coli*.

Figures 5, 5A, 5B:
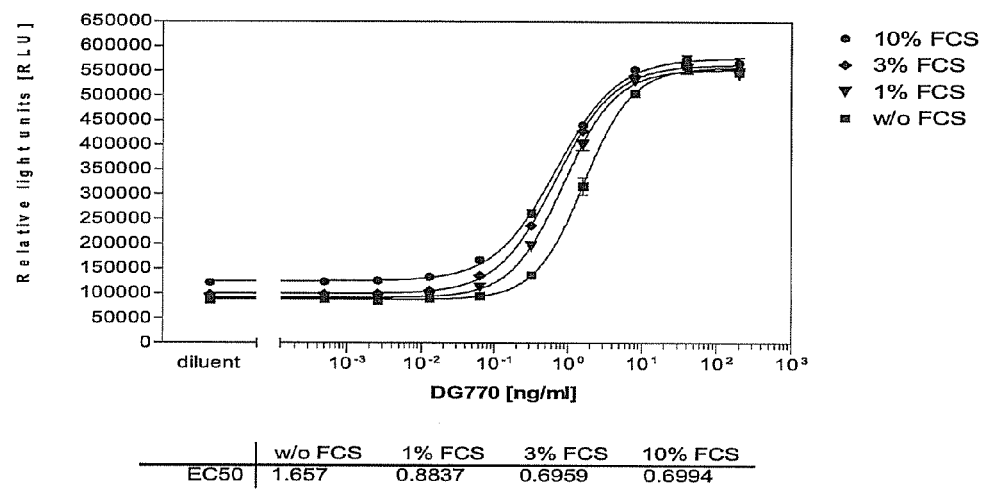

FIGS. 5A and 5B: Quantification of Biological Activity of Neurturin. FIG. 5A. Cellular neurturin biological activity assay: Tyrosine hydroxylase reporter gene activity stimulated by exogenous human recombinant neurturin from *E. coli* in increasing concentrations combined with increasing serum concentrations. FIG. 5B. Biological activity of neurturin variants (n.d.: not detected)

FIG. 6: Alignment of neurturin sequences from different vertebrate species. Amino acids 47-69 of mature human neurturin (SEQ ID NO: 8) are shown (numbering of the positions according to the sequence of mature human neurturin peptide, genbank accession number NP_004549, mature peptide as 96-197). Amino acid variations different to human neurturin are printed bold and underlined (GenBank Accession Numbers in brackets). Several non-human neurturin amino acid sequences corresponding to amino acids 47-69 of mature human neurturin are depicted, including the sequences from *Macaca mulatta* (SEQ ID NO: 9); *Bos tauros* (SEQ ID NO: 10); *Canis familiaris* (SEQ ID NO: 11); *Mus musculus* (SEQ ID NO: 12); *rattus norvegicus* (SEQ ID NO: 13); *Ornithorhnchus anatinus* (SEQ ID NO: 14); *Monodelphis domestica* (SEQ ID NO: 15) and *Gallus gallus* (SEQ ID NO: 16).

FIGS. 7A-7B: DNA Sequence of a Neurturin Expression Construct: Kr-G3-H6-G3-Xa-Rhneurturin (wt). Kr-G3-H6-G3-Xa-rhneurturin(wt) cloned into pMA vector. The DNA-sequence of the sense (SEQ ID NO: 17) and the anti-sense strand (SEQ ID NO: 18) are shown together with restriction sites and the resulting amino-acid sequence (SEQ ID NO: 19) of the coding region.

Figure 8:
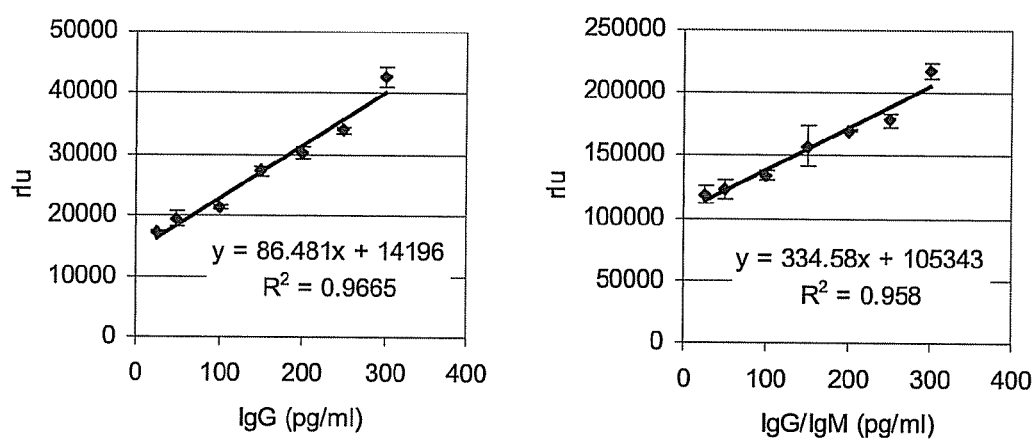
Figure 9:
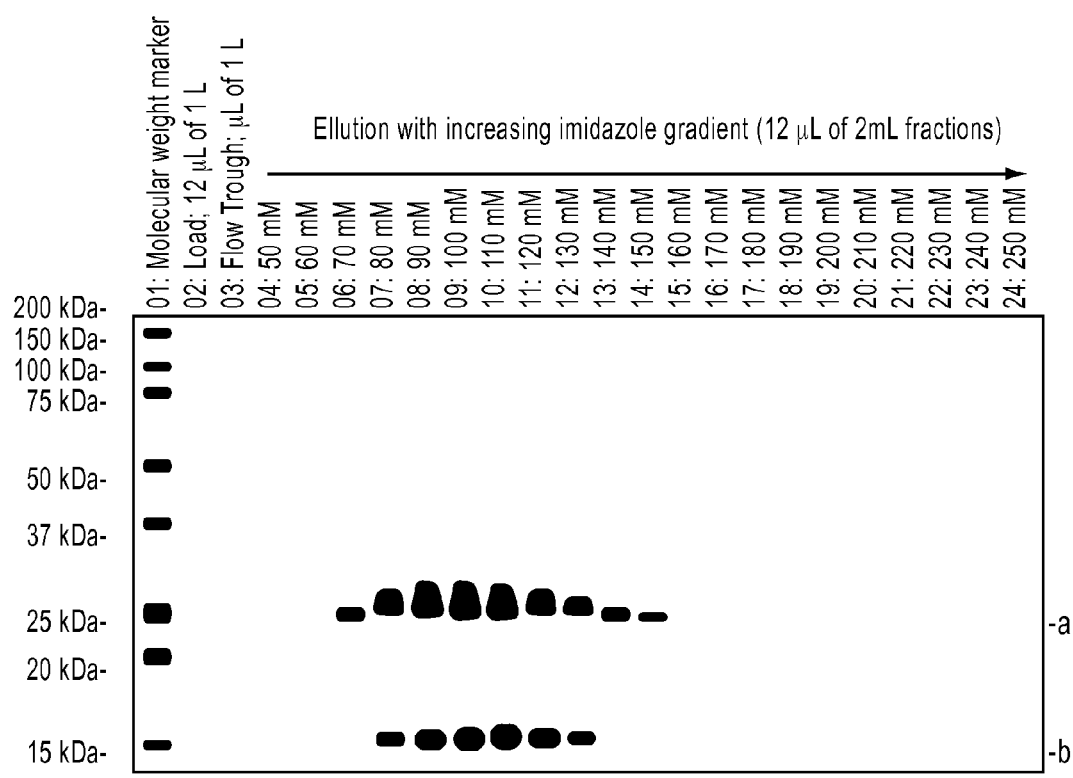

FIG. 8: Anti-Neurturin Antibody ELISA. Anti-neurturin antibody ELISA: left: Standard curve using anti-neurturin IgG, right: Standard curve using anti-neurturin IgG/IgM FIG. 9: Capture and Purification of $G_3H_6G_3Xa$-rhNTN (R63K). HEK293 cells were transfected with the pcDNA 3.1+ Kr-$G_3H_6G_3Xa$-rhNTN(R63K) expression vector and cultured for 4 days in a volume of 1 L. The expressed $G_3H_6G_3Xa$-rhNTN(R63K) was captured and purified by immobilized nickel ion chromatography. Non-reducing SDS-PAGE and coomassie blue protein stain of the load (lane 02), the flow through (lane 03) and the eluted fractions (lanes 04-24) containing $G_3H_6G_3Xa$-rhNTN(R63K) in dimeric (a) or monomeric (b) form with an apparent MW of 23.6 and 13.3 kDa, respectively, are shown. The apparent molecular mass is judged by comparison with a molecular weight marker (lane 1).

Figure 10:
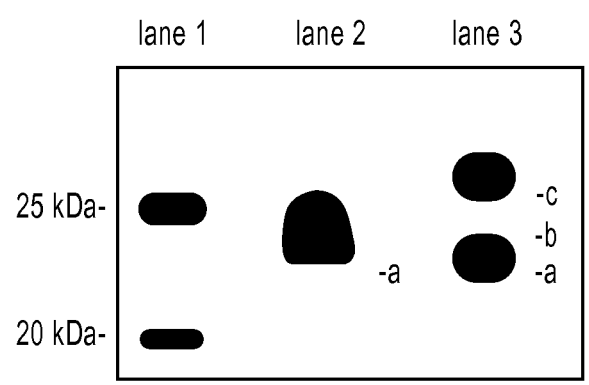

FIG. 10: PEGylation of $G_3H_6G_3Xa$-rhNTN(R63K) Purified $G_3H_6G_3Xa$-rhNTN(R63K) was PEGylated with NHS-PEG with a MW of 2 kDa and subsequently cleaved with Protease Xa to remove the $G_3H_6G_3Xa$-tag leaving PEGylated rhNTN(R63K). Non-reducing SDS-PAGE and Coomassie blue protein stain of the PEG-free control reaction (lane 2) and the PEG-containing reaction (lane 3) are shown. The apparent molecular mass is judged by comparison with a molecular weight marker (lane 1). The different rhNTN (R63K) fractions are indicated: non-PEGylated rhNTN (R63K) dimer (a), mono-PEGylated rhNTN(R63K-PEG) dimer (b), and di-PEGylated rhNTN dimer (R63K-$PEG_2$) (c).

DETAILED DESCRIPTION OF THE INVENTION

The present invention provides neurturin conjugates comprising covalently attached polyol moieties such as polyethylene glycol (PEG), as well as pharmaceutical compositions comprising these neurturin conjugates, as well as variants, derivatives or biologically active fragments thereof.

Unless specific definitions are provided, the nomenclature utilized in connection with, and the laboratory procedures, techniques and methods described herein are those known in the art to which they pertain. Standard chemical symbols and abbreviations are used interchangeably with the full names represented by such symbols. Standard techniques may be used for chemical syntheses, chemical analyses, pharmaceutical preparation, composition, delivery, and treatment of patients. Standard techniques may be used for recombinant DNA methodology, oligonucleotide synthesis, tissue culture and the like. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification.

The term "analog" refers to a polypeptide which resembles neurturin in structure, having a similar function.

The term "biologically active" or "biologic activity" as used herein means that the neurturin product induces and/or stimulates the differentiation of insulin producing cells from progenitor, e.g. stem cells, and/or promotes the protection, survival, or regeneration of insulin producing cells, e.g. beta cells in vivo or in vitro. The biologic activity of the modified neurturin protein products as disclosed herein can easily be determined in standard in vitro assays as disclosed for the determination of GDNF activity, described in WO 93/06116 and in U.S. patent application Ser. No. 08/535,681 or as described in the present Examples.

As used herein, "fragments" of neurturin refer to portions of neurturin that are generated by any method, including but not limited to enzymatic digestion and chemical cleavage (e.g. CNBr) of neurturin and physical shearing of the polypeptide. Fragments of neurturin may also be generated, e.g. by recombinant DNA technology and by amino acid synthesis.

As "active fragment" or "biologically active fragment" of neurturin as used in the present invention refers to any fragment or precursor of the polypeptidic chain of neurturin, alone or in combination with related molecules or residues bound to it, for example, residues of sugars or phosphates, or aggregates of the polypeptide molecule when such fragments or precursors show the same biological activity of neurturin. The term "biologically active fragment" also relates to a fragment of a neurturin product which induces and/or stimulates the differentiation of insulin producing cells from progenitor, e.g. stem cells, and/or promotes the protection, survival, or regeneration of insulin producing cells, e.g. beta cells in vivo or in vitro. The biologic activity of a fragment of the modified neurturin protein products as disclosed herein can easily be determined in standard in vitro assays as disclosed for the determination of GDNF activity, described in WO 93/06116 and in U.S. patent application Ser. No. 08/535,681 or as described in the present Examples.

The term "homologue" is used herein to relate to a polypeptide related to neurturin by descent from a common ancestral protein sequence. The term, homolog, may apply to the relationship between proteins separated by the event of genetic duplication.

The term "low molecular weight substance" refers to a substance with an average molecular weight of between 100 and 12000 Da, preferably of between 200 and 8000 Da and most preferably of about 500 and 7000 Da.

The low molecular weight substance may be a polyanionic polymer which is natural or synthetic and which contains a plurality of anionic groups such as carboxylate and/or sulfate groups. For example, the polyanionic polymer may be selected from low molecular weight sulphated saccharides, sulphated cyclodextrins, or sulphated synthetic polymers such as acrylic polymers, aromatic polymers, and/or polyalcohols. More particularly, the polyanionic polymer is selected from low molecular weight heparins or heparin derivatives, heparan sulphates, chondroitin sulfates, dextran sulphates, chemically modified heparin-derived oligosaccharides (list from Wang et al. (2002), supra), heparin-like oligosaccharides, dextran sulphates, sulphated low molecular weight glycosaminoglycans, dextrin-2-sulphates, cellulose sulphates and naphthalene sulfonate polymer (e.g. PRO 2000), PAVAS (a co-polymer of acrylic acid with vinyl alcohol sulphate), the sulphonated polymer PAMPS [poly(2-acryl-amido-2-methyl-1-propanesulfonic acid] ($M_w$ e.g. approximately 7000-12000), chondroitin sulphates, sulphated cyclodextrins, laminarin sulphate (Alban, S. in *Carbohydrates in Drug Design* (Ed. Z. J. Witczak, K. A. Nieforth) Dekker, New York, 1997, pp 209.), polyglycerin sulphates (Türk, H., Haag, R., Alban, S. *Bioconjugate Chem.* 2004, 15, 162;), pentosan polysulphates (PPS) and derivatives thereof such lactose-modified pentosan polysulphates, fractionated PPS/low molecular weight PPS, fucoidan, or derivatives or combinations thereof.

Low molecular weight heparin (LMWH) analogues such as Enoxaparin, Dalteparin or Fragmin are preferred examples of suitable polymers. They are obtained by fractionation and/ or limited enzymatic or chemical digestion of heparin, and have an average molecular weight of preferably about 3000 to about 7000 Dalton (Weitz 1997 supra).

The term "modified neurturin protein product" as used herein relates to a chemically modified neurturin protein conjugate as well as cell-expressed conjugate comprising a covalently attached polyol moiety.

Chemically modified neurturin conjugates may be prepared by one of skill in the art given the disclosures herein or by any of the methods known in the art.

The polyol moiety of the neurturin conjugate of the invention can be any water-soluble mono- or bifunctional poly (alkylene oxide) having a linear or branched chain. Typically, the polyol is a poly(alkylene glycol) such as poly(ethylene glycol) (PEG). However, those of skill in the art will recognize that other polyols, such as, for example poly(propylene glycol) and copolymers of polyethylene glycol and polypropylene glycol, can be suitably used. Other neurturin conjugates can be prepared by coupling neurturin to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used.

The protein conjugates may also be expressed in prokaryotic or eukaryotic cells well known in the art.

The term "neurturin conjugate" relates to a neurturin protein product which comprises a polyol moiety such as polyethylene glycol covalently attached to an amino acid of neurturin. The amino acid can be site-specific at the N-terminal amino acid or at any other amino acid. PEG conjugates can contain one or more PEG molecules covalently attached to any suitable site of the neurturin protein molecule.

The term "neurturin protein product", "neurturin product", "neurturin protein" or "neurturin" which are used interchangeably herein, relate to a protein or peptide having a degree of identity to the biologically active human neurturin product resulting in the cleavage of the neurturin precursor having the amino acid sequence published as GenBank Accession Number NP_004549 (SEQ ID NO: 1, FIG. 3) or to the human neurturin precursor itself, that is in excess of 70%, preferably in excess of 80%, more preferably in excess of 90% and most preferably in excess of 95%, variants or derivatives thereof. The degree of identity between the mouse and the human protein is about 91%, and it is contemplated that preferred mammalian neurturin proteins will have a similarly high degree of identity. The percentage of identity of a neurturin product and the human neurturin protein or a precursor may be determined according to standard procedures, e.g. by using the BLAST algorithm. Preferably, the percentage of identity is calculated as the percentage of amino acid residues found in the smaller of the two sequences that align with identical amino acid residues in the sequence being compared, when four gaps in a length of 100 amino acids may be introduced to assist in that alignment.

The term "ortholog" relates to polypeptides in different species that evolved from a common ancestral gene by specification. Orthologs retain the same function in the course of evolution.

The term "polyethylene glycol" or "PEG" relates to PEG itself as well as derivatives thereof. The polymer PEG is commonly used as methoxy-PEG-OH, (m-PEG), in which one terminus is the relatively inert methoxy group, while the other terminus is a hydroxyl group that is subject to chemical modification. Branched PEGs are also in common use. The number of branching arms (m) can range from three to a hundred or more. The hydroxyl groups are further subject to chemical modification. Another branched form, such as that described in PCT patent application WO 96/21469, has a single terminus that is subject to chemical modification. Yet another branched form, has reactive groups, such as carboxyl, along the PEG backbone rather than at the end of PEG chains. In addition to these forms of PEG, the polymer can also be prepared with weak or degradable linkages in the backbone. For example, Harris has shown in U.S. patent application Ser. No. 06/026,716, which is incorporated by reference herein in its entirety, that PEG can be prepared with ester linkages in the polymer backbone that are subject to hydrolysis. This hydrolysis results in cleavage of the polymer into fragments of lower molecular weight. The copolymers of ethylene oxide and propylene oxide are closely related to PEG in their chemistry, and they can be used instead of PEG in many of its applications.

The term "PEGylation" comprises covalent attachment of a polyethylene glycol molecule to a substrate, which can be a protein. PEGylation of proteins is widely known in the state of the art and has been reviewed by, for example, Veronese, F. M., Biomaterials 22 (2001) 405-417. PEG can be linked using different functional groups and polyethylene glycols with different molecular weight, linear and branched PEGs as well as different linking groups (see also Francis, G. E., et al., Int. J. Hematol. 68 (1998) 1-18; Delgado, C., et al., Crit. Rev. Ther. Drug Carrier Systems 9 (1992 (249-304). PEGylation can be performed in aqueous solution with PEGylation reagents as described, for example, in WO 00/44785, preferably using NHS-activated linear or branched PEG molecules of a molecular weight between 5 and 40 kDa. PEGylation can also be performed at the solid phase according to Lu, Y. et al., Reactive Polymers 22 (1994) 221-229.

Selective PEGylation at the N-terminal amino acid can be performed according to Felix, A. M., et al., ACS Symp. Ser 680 (Poly(ethylene glycol)) (1997) 218-238. Selective N-terminal PEGylation is achieved during solid-phase synthesis by coupling of a N-PEGylated amino acid derivative to the N-terminal amino acid of the peptide chain. Side chain PEGylation is performed during solid-phase synthesis by coupling of N-PEGylated amino acid derivatives to the growing chain. Combined N-terminal and side chain PEGylation is processed either as described above within solid-phase synthesis or by solution phase synthesis by applying activated PEG reagents to the amino deprotected peptide.

Suitable PEG derivatives are activated PEG molecules with a preferred average molecular weight of from about 5 to about 40 kDa, more preferably from about 20 to about 40 kDa, and most preferably about 30 kDa. In other embodiments, PEG derivatives with a preferred average molecular weight of from about 1 to about 5 kDa, more preferably from about 1.5 to about 3 kDa, and most preferably about 2 kDa are used. The PEG derivatives can be linear or branched PEGs.

Activated PEG derivatives are known in the art and described in, for example, Morpurgo, M., et al., J. Bioconj. Chem. 7 (1996) 363-368, for PEG-vinylsulfone. Linear chain and branched chain PEG species are suitable for the preparation of the PEGylated conjugates. Examples of reactive PEG reagents have the structure RO-(PEG)$_m$-X, e.g. iodo-acetyl-methoxy-PEG, methoxy-PEG-vinylsulfone or methoxy-PEG-carboxylic acid active ester, e.g. succinimidyl ester. X is a reactive group for coupling to amino acid side chains, e.g. $NH_2$, OH, $CO_2H$ side chains, or to the N- or C-terminus, m is preferably an integer from about 100 or 450 to about 900 and R is lower alkyl, linear or branched, having one to six carbon atoms such as methyl, ethyl, isopropyl, etc., from which methyl is preferred.

As used herein, the term "PEG" or "PEG moiety" is intended to include, but is not limited to, linear and branched PEG, methoxy PEG, hydrolytically or enzymatically degradable PEG, pendant PEG, dendrimer PEG, copolymers of PEG and one or more polyols, and copolymers of PEG and PLGA (poly(lactic/glycolic acid)).

The term "PEGylated neurturin" or neurturin modified by "PEGylation" or "neurturin conjugate comprising a polyethylen glycol moiety" relates to a neurturin protein product produced by a method by which a PEG moiety is covalently attached to form these PEGylated proteins.

The term "pharmaceutically acceptable carrier, diluent and/or adjuvant" relates to one and more pharmaceutically and physiologically acceptable compounds such as excipients and auxiliaries, which facilitate processing of the active ingredient(s) into preparations, which can be used pharmaceutically. Details may be found in the latest edition of Remington's Pharmaceutical Sciences (Maack Publishing Co., Easton, Pa.).

The term "unmodified control neurturin protein product" relates to a neurturin protein product of the same origin as the correlating modified neurturin protein product which is used as a control.

The term "variant" as used herein relates to a polynucleotide variant which may contain one or more substitutions, additions, deletions and/or insertions, as further described below, relative to a native polypeptide. The term "variant" also encompasses homologous polypeptides of xenogenic origin. Typically, a neurturin variant retains biological activity either completely, a substantial proportion thereof, or at least partially as, for example, can be determined using a specific assay as described below. The term "variant" as used herein also encompasses neurturin which was modified by altering the protein sequences by substitutions, additions or deletions providing functionally equivalent molecules, as is well known in the art. The latter includes altered sequences in which functionally equivalent amino acid residues are substituted by residues within the sequence resulting in a biologically silent exchange.

Neurturin variants are prepared by introducing appropriate nucleotide changes into the DNA encoding the polypeptide or by in vitro chemical synthesis of the desired polypeptide. It will be appreciated by those skilled in the art that deletions, insertions, and substitutions can be made, resulting in a protein product variant presenting neurturin biological activity.

Mutagenesis techniques for such a substitution, insertion or deletion of one or more selected amino acid residues are well known to one skilled in the art (e.g., U.S. Pat. No. 4,518,584, the disclosure of which is hereby incorporated by reference.)

In a preferred embodiment, amino acid changes are introduced into the region between amino acids 47-69, preferably 51-65, of mature human neurturin (amino acids 141-164, preferably 147-160 as shown in FIG. 3). These amino acid changes may comprise at least one deletion or substitution of an arginine residue in this region, e.g. arginine residues 51, 52, 54, 56, 57, 58, 60, 61, 63 and/or 65. Preferred are substitutions of arginine by neutral or acidic amino acids, e.g. glycine, serine, alanine, aspartate or glutamate. Especially preferred is a substitution by glutamate, e.g. R51E, R52E, R54E, R56E, R57E, R58E, R60E, R61E, R63E and R65E or a neurturin variant comprising at least 2 of these substitutions.

Alternatively and/or additionally an amino acid residue of neurturin, e.g. in the above-indicated region, particularly an arginine residue, may be substituted by lysine in order to facilitate coupling to polyol groups. As there is no lysine in mature human neurturin, such a change allows site-specific modification with polyol groups. Especially preferred is a substitution by lysine in the above-indicated region, e.g. R51K, R52K, R54K, R56K, R57K, R58K, R60K, R61K, R63K and R65K or a neurturin variant comprising at least 2 or more of these substitutions.

In one particular embodiment, the arginine residue 63 is deleted or substituted. The arginine residue 63 may be substituted by neutral or acidic amino acids as described above or by lysine. In a further particular embodiment, the arginine residue 63 is substitued by lysine. In a further particular embodiment, this neurturin variant is otherwise identical to human mature neurturin or may carry an additional N-terminal methionine.

A neurturin monomer variant into which a lysine residue has been introduced may comprise a single polyol moiety covalently bound to the respective lysine residue or to the N-terminal amino group or 2 polyol moieties, one of them bound to the N-terminal amino group and one bound to the introduced lysine residue. In a particular embodiment, a neurturin monomer conjugate is obtained comprising (i) a single polyol moiety covalently bound to the N-terminus or to a lysine, e.g. lysine 63 or (ii) two polyol moieties, one of them bound to the N-terminus and one bound to or lysine, e.g. lysine 63. These polyol moieties may, e.g. be selected from PEG moieties as described above. These neurturin monomer conjugates may combine to neurturin dimer conjugates which may comprise 1-4 polyol moieties as follows:

(i) a mono-conjugated, e.g. mono-pegylated neurturin variant dimer, consisting of 1 unconjugated monomer and 1 mono-conjugated, i.e. N-terminal or lysine side-chain conjugated monomer, (ii) a di-conjugated, e.g. di-pegylated neurturin variant dimer, consisting of
  1 unconjugated monomer and 1 di-conjugated, i.e. N-terminal and lysine-side chain di-conjugated monomer,
  2 N-terminal mono-conjugated monomers,
  2 lysine side-chain mono-conjugated monomers,
  1 N-terminal mono-conjugated monomer and 1 lysine side-chain mono-conjugated monomer, (iii) a tri-conjugated, e.g. tri-pegylated neurturin variant dimer, consisting of:
  1 N-terminal mono-conjugated monomer and 1 N-terminal and lysine-side chain di-conjugated monomer,
  1 lysine side-chain monoconjugated monomer and 1 N-terminal and lysine-side chain di-conjugated monomer, and (iv) a tetra-conjugated, e.g. tetra-pegylated neurturin variant dimer, consisting of
  2 N-terminal and lysine-side chain di-conjugated monomers.

The present invention also encompasses mixtures of mono-, di-, tri-, and/or tetra-conjugated neurturin dimers as described above.

Neurturin substitution variants have at least one amino acid residue of the human or mouse neurturin amino acid sequence removed and a different residue inserted in its place. Such substitution variants include allelic variants, which are characterized by naturally occurring nucleotide sequence changes in the species population that may or may not result in an amino acid change.

Surprisingly, it was found by the present inventors that a pharmaceutical composition as disclosed has an increased bioavailability of its active ingredient, said conjugated neurturin and/or biologically active fragment thereof, compared to a pharmaceutical composition comprising no conjugated neurturin. The invention demonstrates that the conjugation of neurturin protein to a polyol such as PEG improves significantly the serum half life and bioavailability of a neurturin product. Improvement of the bioavailability of a neurturin product in turn may reduce accumulation or processing of the agent at the injection site if applied subcutaneously and may improve local tolerance this way.

The present invention provides for a method of applying the inventive neurturin conjugates as active agents to patients in a much lower dose compared to unmodified control neurturin in order to have a therapeutic effect. This complies with the need for "user-friendly protein therapeutics" and may also result in lower costs for producing active agent and/or pharmaceutical composition.

The present neurturin conjugates also have a higher solubility in aqueous solutions compared to unmodified neurturin which may result in a simplification of formulating the active agent.

As a further advantage, coupling polyols such as PEG to neurturin may reduce immunogenicity to neurturin and therefore the formation of neutralizing antibodies or allergic reactions against the active agent.

Preferably, the neurturin protein product of the present invention is a human neurturin or a biologically active fragment thereof. Neurturin protein products are preferably produced via recombinant techniques because such methods are capable of achieving high amounts of protein at a great purity, and are not limited to products expressed in bacterial, plant, mammalian, or insect cell systems.

Recombinant neurturin protein products include glycosylated and non-glycosylated forms of the protein. In general, recombinant techniques involve isolating the genes encoding a neurturin protein product, cloning the gene in a suitable vector and/or cell type, modifying the gene if necessary to encode a desired variant, and expressing the gene in order to produce the neurturin protein product.

Alternatively, a nucleotide sequence encoding the desired neurturin product may be chemically synthesized. It is contemplated that a neurturin product may be expressed using nucleotide sequences that vary in codon usage due to the degeneration of the genetic code or allelic variations or alterations made to facilitate production of the protein product by the selected cell.

Kotzbauer et al., Nature 384:467-470, describe the identification of a mouse cDNA and amino acid sequence and a human cDNA and amino acid sequence for a neurturin protein, identified herein as SEQ ID NO: 1.

The neurturin products according to the present invention may be isolated or generated by a variety of means. Exemplary methods for producing neurturin products are described in patent application WO 97/08196, which is hereby incorporated by reference. Also described therein are a variety of vectors, host cells, and culture growth conditions for the expression of neurturin protein, as well as methods to synthesize variants of neurturin protein product. Additional vectors suitable for the expression of neurturin protein product in *E. coli* are disclosed in Patent No. EP 0 423 980, the disclosure of which is hereby incorporated by reference.

The biologically active form of the protein neurturin is a disulfide-bonded dimer which can be determined by the molecular weight of purified neurturin. The material isolated after expression in a bacterial system is essentially biologically inactive, and exists as a monomer. Refolding is necessary to produce the biologically active disulfide-bonded dimer. Processes suitable for the refolding and maturation of the neurturin expressed in bacterial systems are substantially similar to those described in WO 93/06116. Standard in vitro assays for the determination of neurturin activity are also substantially similar to those determining GDNF activity as described in WO 93/06116 and in U.S. patent application Ser. No. 08/535,681, and are hereby incorporated by reference.

Covalent attachment of the inert, non-toxic, big-degradable polymer polyethylene glycol (PEG), also known as polyethylene oxide (PEO), to neurturin has important applications in biotechnology and medicine. PEGylation of neurturin results in improved pharmacokinetics resulting in sustained duration, improve safety (e.g. lower toxicity, immunogenicity and antigenicity), increase efficacy, decrease dosing frequency, improve drug solubility and stability, reduce proteolysis, and facilitate controlled drug release.

The present invention contemplates use of neurturin protein products, e.g. derivatives which are prokaryote-expressed neurturin, or variants thereof, linked to at least one polyethylene glycol molecule, as well as use of neurturin, or variants thereof, attached to one or more polyethylene glycol molecules via an acyl or alkyl linkage. PEGylation may be carried out by any of the pegylation reactions known in the art. See, for example: Focus on Growth Factors, 3 (2):4-10, 1992; EP 0 154 316, the disclosure of which is hereby incorporated by reference; EP 0 401 384; and the other publications cited herein that relate to PEGylation.

The pharmaceutical composition of the present invention preferably comprises a neurturin conjugate as described above, which is present as a dimer, preferably as a dimer of two neurturin monomer conjugate molecules comprising 1-4 polyol, e.g. polyethylene glycol, modifications, e.g. as described above.

The pharmaceutical composition of the present invention has an increased bioavailability of the active ingredient in a mammal, e.g. a human, compared to a pharmaceutical composition which does not contain the PEGylated neurturin (see FIG. 2). Preferably, the PEGylated neurturin is present in an amount to provide an at least 2-fold, preferably at least 5-fold and more preferably at least 10-fold increase in the bioavailability of the active ingredient.

The increase of bioavailability may be determined as shown in the Examples of the present application. More particularly, a composition containing the active ingredient in a given amount or dose is compared to a pharmaceutical composition containing the active ingredient in the same dose but without PEGylation. The bioavailability of both compositions may be determined from the plasma concentration after subcutaneous administration to experimental animals, e.g. mice. Preferably, the plasma-concentration is measured over a time period of at least 120 min, preferably of 240 min and most preferably of 24 h (see FIG. 2).

The pharmaceutical composition of the present invention may be adapted for administration by any effective route, e.g. by oral, nasal, rectal, pulmonal, topical, transdermal or parenteral routes of administration. Thus, the composition may be a solid or liquid composition, e.g. a tablet, capsule, powder, cream, gel, ointment, solution, emulsion, suspension, lyophilisate etc. Preferably, however, the composition is administered by injection or infusion, more preferably by injection, e.g. by subcutaneous or intravenous injection. The pharmaceutical composition is preferably an aqueous solution.

In addition to the active ingredient and optionally low molecular weight substance such as a polyanionic polymer, the pharmaceutical composition may comprise a pharmaceutically acceptable carrier, diluent and/or adjuvant, such as buffers, agents for adjusting tonicity, stabilizers, fillers, disintegrants, thickeners, etc.

The pharmaceutical composition contains the active ingredient in a therapeutically effective amount or dose. The therapeutically effective dose depends on the type of the active ingredient, the type and the variety of the disease to be treated and the type of administration. For parenteral compositions containing neurturin as an active ingredient, the therapeutically effective dose is preferably in the range of about 0.001 mg to 500 mg, more preferably from about 0.05 to about 100 mg, most preferably from about 0.01 to about 5 mg per day.

The composition is preferably administered to a mammal, particularly a human. Thus, the composition is suitable for human and veterinary medicine. The composition is particularly suitable for the prevention and/or treatment of neurodegenerative or pancreatic disorders, particularly pancreatic autoimmune disorders such as diabetes type I and LADA, or diabetes type II.

The neurturin conjugate as described herein may be administered by any suitable means, preferably enterally or parenterally or topically directly to the pancreas, as known to those skilled in the art. The specific dose may be calculated according to considerations of body weight, body surface area or organ size. Further refinement of the calculations necessary to determine the appropriate dosage for treatment involving each of the above mentioned compositions is routinely made by those of ordinary skill in the art and is within the ambit of tasks routinely performed. Appropriate dosages may be ascertained through use of the established assays for determining dosages utilized in conjunction with appropriate dose-response data. The final dosage regimen involved in a method for treating the above described conditions will be determined by the attending physician, considering various factors which modify the action of drugs, e.g., the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of a neurturin conjugate as described herein may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein having the effect of continuous presence, in predictable amounts, based on a determined dosage regimen. Thus, neurturin protein products include proteins derivatized or otherwise formulated to effectuate such continuous administration.

In a further preferred embodiment, neurturin conjugate can be delivered directly to progenitor, e.g. stem cells in order to stimulate the differentiation of insulin producing cells in vitro or in vivo. In this embodiment of the invention, neurturin conjugate may be added preferably at concentrations between 0.1 ng/ml and 500 ng/ml, more preferably between 1 ng/ml and 100 ng/ml, even more preferably between 20 and 80 ng/ml and most preferably 50 ng/ml.

The neurturin conjugate as disclosed herein may be used either in a monotherapy or in a combination therapy with other pharmaceutical agents. For example, it may be administered together with other pharmaceutical agents suitable for the treatment or prevention of pancreatic diseases and/or obesity and/or metabolic syndrome, particularly with other pharmaceutical agents suitable for stimulating and/or inducing the differentiation of insulin producing cells from progenitor cells. Further, it may be used together with pharmaceutical agents which have an immunosuppressive activity, e.g. antibodies, polypeptides and/or peptidic or non-peptidic low molecular weight substances as disclosed in WO 2005/51415.

A further embodiment of the present invention is a variant of human neurturin comprising at least one, e.g. 1, 2, 3 or 4 amino acid changes compared to wild-type human neurturin. The variant of human neurturin may contain one or more substitutions, additions, deletions and/or insertions, as described in detail above, relative to the native human polypeptide. Neurturin variants can be prepared as described above.

In a preferred embodiment, amino acid changes are present in the region between amino acids 47-69, preferably 51-65 of mature human neurturin (amino acids 141-164, preferably 147-160 as shown in FIG. 3). These amino acid changes may comprise at least one deletion or substitution of an arginine residue in this region, e.g. arginine residues 51, 52, 54, 56, 57, 58, 60, 61 and/or 65. Preferred are substitutions of arginine by neutral or acidic amino acids, e.g. glycine, serine, alanine, aspartate or glutamate. Especially preferred is a substitution by glutamate, e.g. R51E, R52E, R54E, R56E, R57E, R58E, R60E, R61E, R63E and R65E, or a neurturin variant comprising at least two or more of these substitutions.

Also preferred are variants of human neurturin, wherein alternatively and/or additionally an amino acid residue, e.g. in the above-indicated region, particularly an arginine residue, is substituted by lysine. Thereby, site-specific coupling of the neurturin variant to polyol groups is facilitated. Especially preferred is a substitution by lysine in the above-indicated region, e.g. R51K, R52K, R54K, R56K, R57K, R58K, R60K, R61K, R63K and R65K or a neurturin variant comprising at least 2 of these substitutions.

Neurturin substitution variants according to the present invention have at least one amino acid residue of the human neurturin amino acid sequence removed and a different residue inserted in its place. Such substitution variants include allelic variants which are characterized by naturally occurring nucleotide sequence changes in the species population that may or may not result in an amino acid change.

The present invention further provides a method for administering a pharmaceutical composition to a subject in need thereof, wherein said composition comprises a pharmaceutically active amount or dose of at least one neurturin protein product conjugated with at least one polyol such as PEG or a biologically active fragment of such conjugated neurturin as an active ingredient together with a pharmaceutically acceptable carrier, diluent and/or adjuvant.

The invention even further provides a method for administering a pharmaceutical composition to a subject in need thereof, wherein said composition comprises a pharmaceutically active amount or dose of at least one modified neurturin protein product or a biologically active fragment thereof as an active ingredient together with a low molecular weight substance together with a pharmaceutically acceptable carrier, diluent and/or adjuvant.

FIGURES

The following Figures and Examples illustrate the invention and are non-limiting embodiments of the invention as claimed below. Numerous additional aspects and advantages of the invention will become apparent to those skilled in the art upon consideration of the following description of the Figures.

FIG. 1: Biological Activity of PEGylated Neurturin in Cell Culture

Figure 1A:
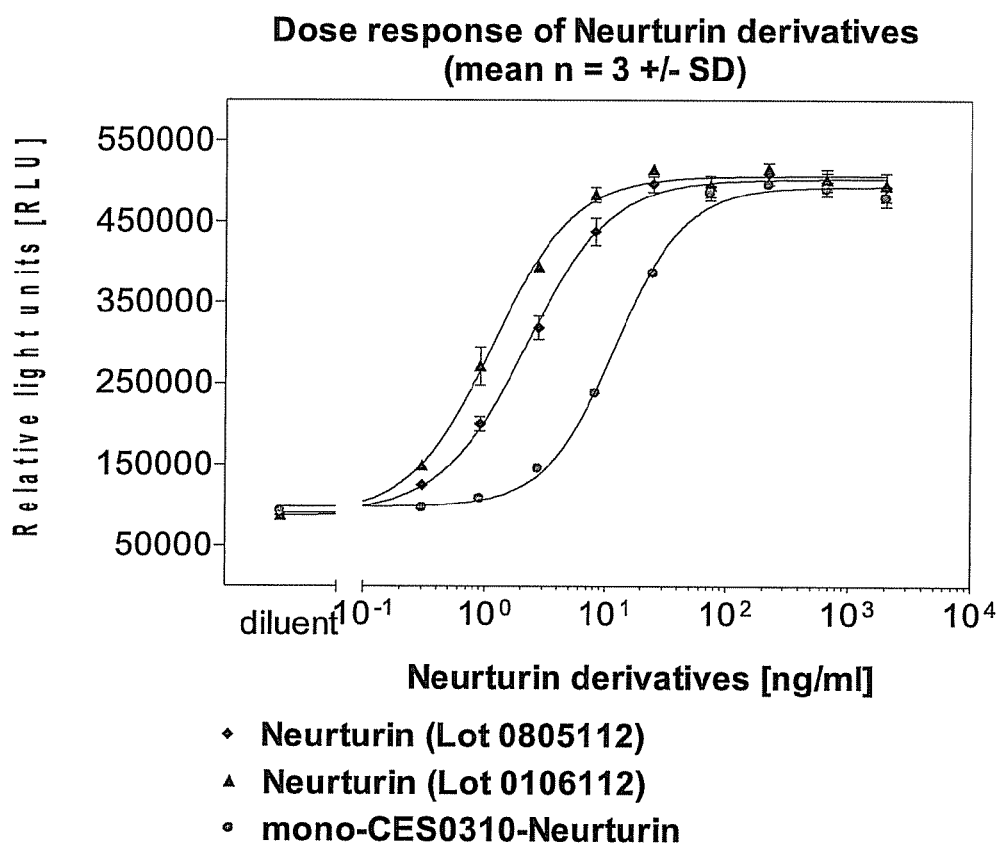
FIGS. 1A and 1B: Biological Activity of PEGylated Neurturin in Cell Culture
Figure 1B:
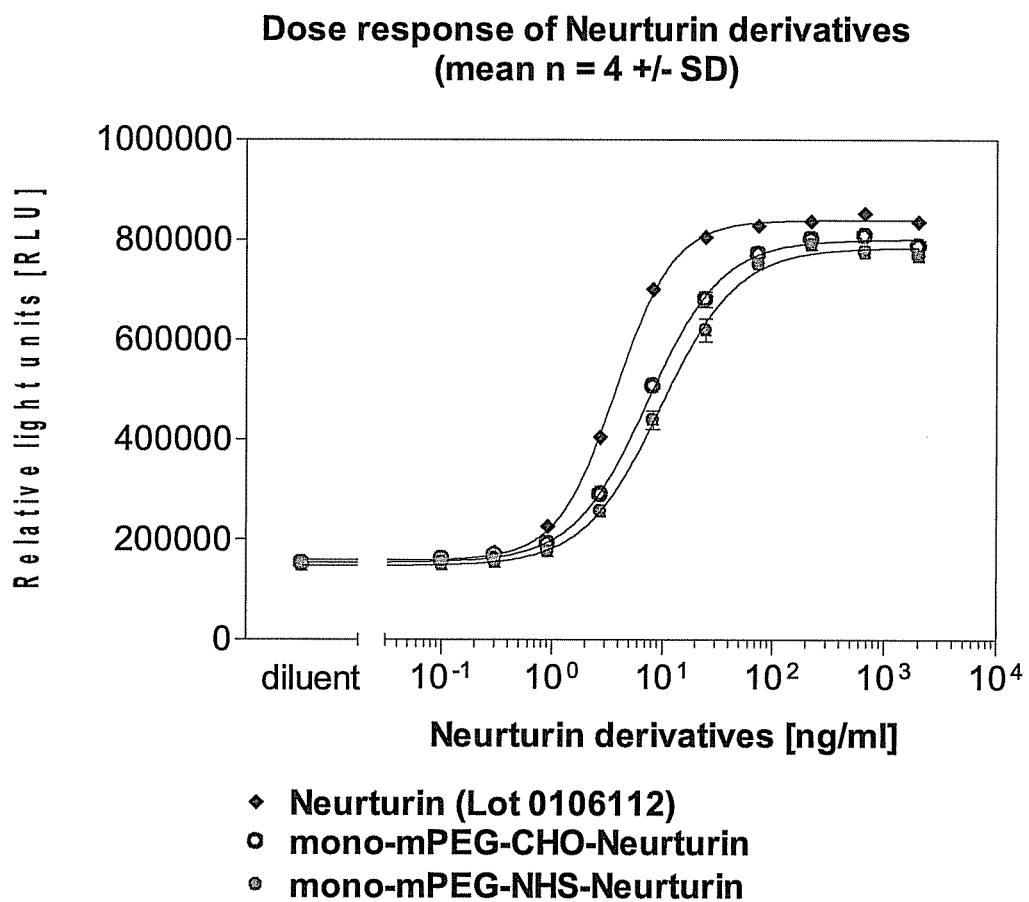

The reporter cell line was subjected to increasing concentrations of neurturin or neurturin conjugated with PEG (PEGylated neurturin). The resulting reporter gene activity (relative light units (RLU) given on the y-axis) was plotted against the final concentration of the test agent (given on the x-axis in ng/ml; FIGS. 1A and B). Two independently produced batches of unmodified neurturin were used as experimental controls (PeproTech; Lot0805112 and Lot0106112) and their relative activity was compared to those of the three PEGylated conjugates (mono-mPEG-NHS-neurturin, mono-mPEG-CHO-neurturin and mono-CES0310-neurturin). Given values are means of at least 3 wells±S.D. The calculated $EC_{50}$ of the various tests are: Neurturin (Lot0805112, unmodified protein): $EC_{50}$=2.2 ng/ml, neurturin (Lot0106112, unmodified protein): $EC_{50}$=1.2 ng/ml, mono-CES0310-neurturin: $EC_{50}$=12 ng/ml (FIG. 1A), and neurturin (Lot0106112, unmodified protein): $EC_{50}$=3.8 ng/ml, mono-mPEG-NHS-neurturin: $EC_{50}$=9.7 ng/ml, and mono-mPEG-CHO-neurturin: $EC_{50}$=7.4 ng/ml (FIG. 1B).

Figure 2A:
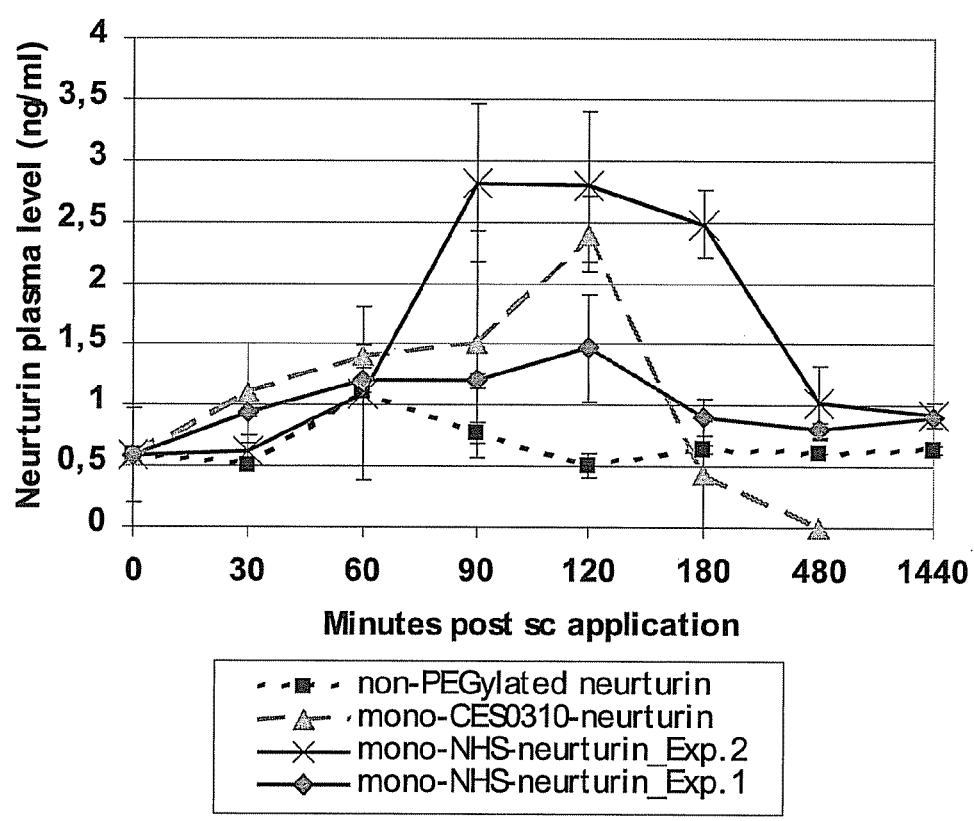
FIGS. 2A and 2B: Pharmacokinetic (PK) Studies After Subcutaneous Administration of Test Agents in Mice
Figure 2B:
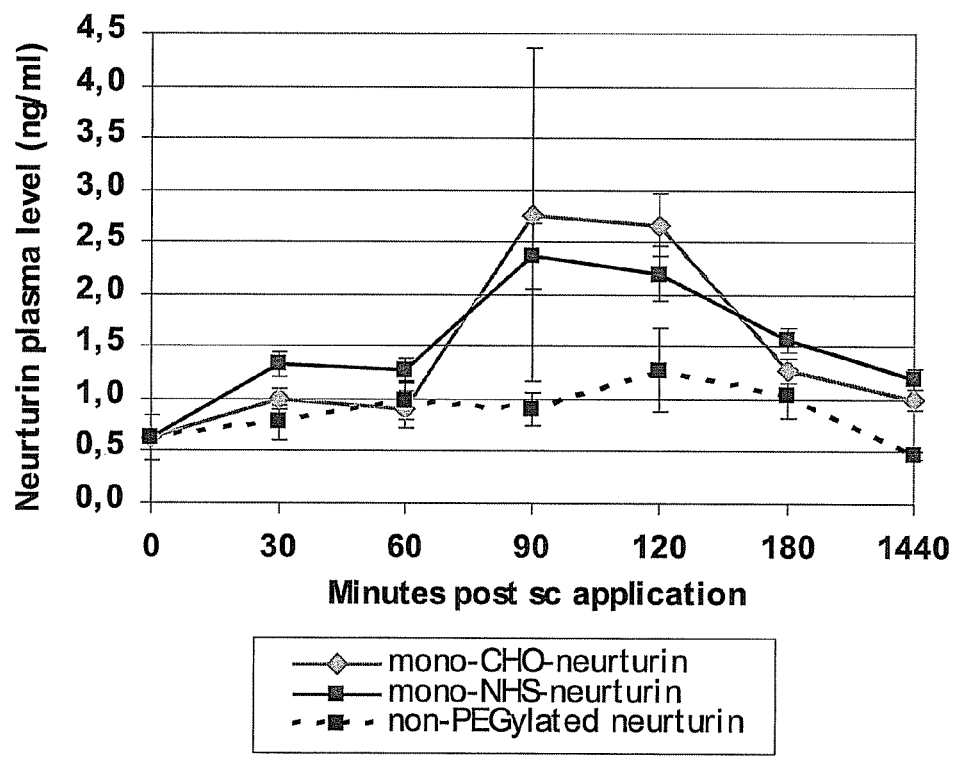

FIG. 2: Pharmacokinetic (PK) Studies After Subcutaneous Administration of Test Agents in Mice FIGS. 2A and B show the neurturin plasma concentrations in ng/ml at various time points after the administration of 0.050 mg/kg BW (FIG. 2A) or 0.50 mg/kg BW (FIG. 2B) neurturin or PEGylated neurturin to mice. Resulting plasma levels were determined by a neurturin ELISA assay. Time point zero shows the average background signal for neurturin in mouse serum using this ELISA assay. The background values were calculated from independently measured values from sera of 12 (FIG. 2A) or from 11 (FIG. 2B) untreated mice The other indicated values are means of measured serum levels from three animals±SD. FIG. 2A shows PK data for the neurturin conjugate mono-NHS-neurturin stemming from two independent experiments (mono-NHS-neurturin_Exp.1 and -_Exp.2). FIG. 2B shows data derived from yet another experiment where mice were treated with 0.50 mg/kg BW mono-NHS-neurturin.

For area under the curve (AUC) analysis covering all measured time points, the baseline was set to 0.6 ng/ml (the average background value at the time point 0): Neurturin unmodified protein: 18.8 ng*min/ml, mono-mPEG-NHS-neurturin_Exp1: 409 ng*min/ml, mono-mPEG-NHS-neurturin_Exp2: 918 ng*min/ml, mono-CES0310-neurturin: $EC_{50}$=142 ng*min/ml (FIG. 2A), and neurturin unmodified protein: 324 ng*min/ml, mono-mPEG-NHS-neurturin: 1157 ng*min/ml, and mono-mPEG-CHO-neurturin: 845 ng*min/ml (FIG. 2B).

For the area under the curve (AUC) analysis (FIGS. 2A and B) of neurturin serum levels the baseline was set to 0.6 ng/ml neurturin which corresponds to the average background level determined in the serum of untreated mice.

FIG. 3:

Protein sequence of human neurturin precursor (SEQ ID NO: 1) as published by the National Center for Biotechnology Information (NCBI) (accession number: NP_004549). The sequence of the mature protein (SEQ ID NO: 5) which corresponds to the biologically as well as pharmacologically active form is highlighted in bold.

FIG. 4:

FIG. 4A. Expression of human neurturin and mutated neurturin variants. Native-PAGE/Western-blot of concentrated supernatant from HEK-293 cells expressing neurturin and neurturin variants (numbering of the positions according to the sequence of mature human neurturin, R: arginine, E: glutamic acid).

FIG. 4B. Neurturin ELISA: Representative standard curve using human recombinant neurturin expressed from *E. coli.*

FIG. 5: Quantification of Biological Activity of Neurturin

FIG. 5A. Cellular neurturin biological activity assay: Tyrosine hydroxylase reporter gene activity stimulated by exogenous human recombinant neurturin from *E. coli* in increasing concentrations combined with increasing serum concentrations.

FIG. 5B. Biological activity of neurturin variants (n.d.: not detected)

FIG. 6: Alignment of neurturin sequences from different vertebrate species

Amino acids 47-69 of mature human neurturin (SEQ ID NO: 8) are shown (numbering of the positions according to the sequence of mature human neurturin peptide, genbank accession number NP_004549, mature peptide as 96-197). Amino acid variations different to human neurturin are printed bold and underlined (GenBank Accession Numbers in brackets). Several non-human neurturin amino acid sequences corresponding to amino acids 47-69 of mature human neurturin are depicted, including the sequences from *Macaca mulatta* (SEQ ID NO: 9); *Bos tauros* (SEQ ID NO: 10); *Canis familiaris* (SEQ ID NO: 11); *Mus musculus* (SEQ ID NO: 12); *rattus norvegicus* (SEQ ID NO: 13); *Ornithorhnchus anatinus* (SEQ ID NO: 14); *Monodelphis domestica* (SEQ ID NO: 15) and *Gallus gallus* (SEQ ID NO: 16).

FIG. 7: DNA Sequence of a Neurturin Expression Construct: Kr-G3-H6-G3-Xa-Rhneurturin (wt)

Kr-G3-H6-G3-Xa-rhneurturin(wt) cloned into pMA vector. The DNA-sequence of the sense (SEQ ID NO: 17) and the anti-sense strand (SEQ ID NO: 18) are shown together with restriction sites and the resulting amino-acid sequence (SEQ ID NO: 19) of the coding region.

FIG. 8: Anti-Neurturin Antibody ELISA

Anti-neurturin antibody ELISA: left: Standard curve using anti-neurturin IgG, right: Standard curve using anti-neurturin IgG/IgM FIG. 9: Capture and Purification of $G_3H_6G_3$Xa-rhNTN (R63K)

HEK293 cells were transfected with the pcDNA 3.1+ Kr-$G_3H_6G_3$Xa-rhNTN(R63K) expression vector and cultured for 4 days in a volume of 1 L. The expressed $G_3H_6G_3$Xa-rhNTN(R63K) was captured and purified by immobilized nickel ion chromatography. Non-reducing SDS-PAGE and coomassie blue protein stain of the load (lane 02), the flow through (lane 03) and the eluted fractions (lanes 04-24) containing $G_3H_6G_3$Xa-rhNTN(R63K) in dimeric (a) or monomeric (b) form with an apparent MW of 23.6 and 13.3 kDa, respectively, are shown. The apparent molecular mass is judged by comparison with a molecular weight marker (lane 1).

FIG. 10: FIG. 2: PEGylation of $G_3H_6G_3$Xa-rhNTN(R63K)

Purified $G_3H_6G_3$Xa-rhNTN(R63K) was PEGylated with NHS-PEG with a MW of 2 kDa and subsequently cleaved with Protease Xa to remove the $G_3H_6G_3$Xa-tag leaving PEGylated rhNTN(R63K). Non-reducing SDS-PAGE and Coomassie blue protein stain of the PEG-free control reaction (lane 2) and the PEG-containing reaction (lane 3) are shown. The apparent molecular mass is judged by comparison with a molecular weight marker (lane 1). The different rhNTN (R63K) fractions are indicated: non-PEGylated rhNTN (R63K) dimer (a), mono-PEGylated rhNTN(R63K-PEG) dimer (b), and di-PEGylated rhNTN dimer (R63K-$PEG_2$) (c).

It should be noted that all preferred embodiments discussed for one or several aspects of the invention also relate to all other aspects.

The versatility of the present invention is illustrated, but not limited, by the following Examples.

EXAMPLES

Example 1

PEGylation of Neurturin

Polyethylenglycol groups (PEG) were conjugated to neurturin through a process called PEGylation. This technology is widely used for the modification of therapeutic proteins and the procedure is familiar to anyone skilled in the art. In the present invention, mono-PEGylated neurturin conjugates were produced by linking a single PEG molecule to the N-terminal amino acid of one of the two subunits of the homodimer. Two different conjugates of mono-PEGylated neurturin were produced that differ in size and structure of the attached PEG as well as in the method of production to conjugate the PEG to the protein. The conjugate disclosed as "mono-mPEG-NHS-neurturin" herein was produced using an about 5 kDa linear PEG-reagent (mPEG-succinimidyl succinat; NOF, Japan). This so-called "NHS-method" is the most commonly used method for PEGylation of soluble proteins. Further, a linear 5 kDa polyethylene glycol butyraldehyde (Nektar, 082M0H01) was used to generate the conjugate disclosed as "mono-mPEG-CHO-neurturin". Under specific experimental conditions NHS esters or aldehydes efficiently react with free amino groups of proteins and peptides. In yet another conjugate disclosed as "mono-CES0310-neurturin", the N-terminal amino acid of one chain of the neurturin homodimer was conjugated to a six-arm branched PEG of about 5 kDa using a PEGylation methodology known in the prior art (see, for example, but not limited to, DE 2005 100 04 157.0, EP 1 631 545 A2; WO 04/108634; WO 07/025763; CA 2528667). Neurturin does not contain lysine residues, therefore the PEGylation reactions described above are expected to primarily lead to a N-terminal PEGylation via the reactive amino groups of the N-terminal amino acids of the neurturin homodimer. The quality (size and purity) of the PEGylated products was confirmed using standard biochemical methodology known to anyone skilled in the art.

Example 2

Biological Activity of PEGylated Neurturin Conjugates or Variants Thereof

The biological activity of the neurturin conjugates was evaluated using a cell based reporter assay. It was determined how strong neurturin or its PEGylated conjugates activate a reporter gene construct in a cell line expressing neurturin receptors on the surface. In this assay the activity of both PEGylated neurturin conjugates was found to be reduced 3 to 10 fold relative to that of unmodified neurturin (FIGS. 1A and B).

The human neuroblastoma cell line TGW (JCRB0618) which expresses the receptors for neurturin on the cell surface was stably transfected with a neurturin reporter gene construct. The reporter gene constructs contains a luciferase gene which is among other regulatory elements under the transcriptional control of repetitive serum response elements (SRE). In these cells the expression of luciferase is stimulated in response to the activation of the MAPK pathway, for instance through binding of neurturin to its surface receptors. The assay is carried out in 96 well plates. The luciferase activity was measured by addition of luciferin substrate to the wells and read-out was generated on a Analyst reader (Molecular Devices) operating in the luminescence mode.

Example 3

Improved Bioavailability of PEGylated Neurturin Conjugates or Variants Thereof The relative bioavailability of the PEGylated conjugates of neurturin was estimated with the help of PK studies in mice (FIGS. 2A and B). In these experiments the protein was subcutaneously injected into the neck region of mice. Following, the serum concentration of neurturin was determined at defined time points after the delivery of the protein using a specific neurturin ELISA assay (FIGS. 2A and B). The sensitivity of this neurturin ELISA assay was limited because of relatively high background signals in the presence of mouse serum, as detected by the use of serum from mice that were not treated with neurturin (point zero values). After the injection of 0.050 mg/kg body weight (BW) unmodified neurturin, the neurturin serum levels did not significantly exceed this background level at any time point. On the contrary, when the same amount of PEGylated neurturin was applied a significant increase in serum levels of the injected protein was detected, irrespective of the kind of the PEG modification (FIG. 2A). When the amount of injected unmodified neurturin was increased 10 times (0.5 mg/kg BW) the protein was significantly detected in the serum at time points 60, 90, 120 and 180 minutes (FIG. 2B). Significance of this observation was confirmed using the T-test and p-values<0.05 were calculated. Also, the serum levels of the PEGylated neurturin derivatives given at the 0.5 mg/kg BW dose were a few-fold higher than these of the unmodified protein (FIGS. 2A and B).

The neurturin conjugates presented herein consistently demonstrate higher serum levels relative to those of the unmodified protein. In conclusion, PEGylation of neurturin significantly improves the bioavailability of neurturin.

Example 4

Neurturin Variants

Basic arginine residues that are located within the basic patch of neurturin (amino acids 51-65 of the mature protein) were replaced by acidic glutamic acid residues through site directed PCR-based mutagenesis. Briefly, the coding sequence of mature human neurturin with an additional N-terminal eukaryotic secretion signal peptide was modified by PCR-based mutagenesis using mismatch primers introducing the desired mutations:

R51E, R52E, R54E, R56E, R57E, R58E, R60E, R61E, R63E, or R65E (numbering of the positions according to the sequence of mature human neurturin peptide, Genbank Accession Number NP_004549, mature peptide as 96-197, this sequence is also shown in FIG. 3; R: arginine; E: glutamic acid).

The resulting plasmids were purified and the correctness of the coding sequence was checked by sequencing. The coding sequences were cloned via flanking HindIII and XhoI cloning sites into pCDNA3.1+ vector (Invitrogen Cat. No. V790-20) for eukaryotic expression.

For eukaryotic expression, these vectors as well as empty control vector and GFP expression vector as transfection control were transiently transfected in HEK-293 cells cultured on 175 cm² tissue culture vessels with 25 ml medium, each. Media harvest was performed 48 hours after transfection and the media supernatant was concentrated by the use of ultra-filtration columns to app. 0.4 ml, each.

The expression of wt human neurturin and the mutated variants was first controlled by native-PAGE/Western-blot using neurturin-specific antibodies for detection (see FIG. 4). As control human recombinant neurturin expressed from *E. coli* was used.

FIG. 4A shows that human wild-type neurturin (wt) as well as all modified neurturin variants except R63E were expressed in similar amounts. The apparent mass of the neurturin variants ranged between 20 and 25 kDa similar to wt neurturin.

The yield of expressed neurturin was determined by an ELISA specific for neurturin. Briefly, rabbit anti-neurturin-antibody was coated onto micro-wells for neurturin capture from the neurturin containing concentrated media supernatant. After washing, the captured neurturin was quantified by a luminescence read-out using biotin-conjugated goat anti-neurturin-antibody followed by the use of peroxidase-conjugated streptavidin. Human recombinant neurturin expressed from *E. coli* was used to establish a standard curve (see FIG. 4B).

Furthermore, the biological activity of the expressed neurturin variants were quantified in a specific cellular assay. The assay principle is based on experiments by Tanaka et al., 2002, 2003 (Tanaka M, Xiao H, Kiuchi K. Heparin facilitates glial cell line-derived neurotrophic factor signal transduction. Neuroreport. 2002 Oct. 28; 13(15)1913-6; Tanaka M, Xiao H, Hirata Y, Kiuchi K. A rapid assay for glial cell line-derived neurotrophic factor and neurturin based on transfection of cells with tyrosine hydroxylase promoter-luciferase construct. Brain Res Brain Res Protoc. 2003 May; 11(2):119-22.) showing the induction of a tyrosine hydroxylase (TH) reporter gene construct by neurturin stably expressed in the human TGW neuroblastoma cell line. Briefly, TGW cells over-expressing the tyrosine hydroxylase (TH) reporter gene construct were treated with the neurturin containing samples leading to induction of MAPK pathway by neurturin signaling. The reporter gene constructs contains a luciferase gene under control of repetitive serum response elements (SRE). The expression of luciferase is depending of MAPK pathway activation. The assay is carried out in 96 well plates. neurturin mediated luciferase expression is measured by addition of luciferin and analyzed with a luminescence reader.

A representative experiment demonstrating the quantification of the biological activity of neurturin using human recombinant neurturin expressed in *E. coli* as standard in combination with increasing serum concentrations is shown in FIG. 5A.

FIG. 5B shows that wild-type recombinant human neurturin as well as all neurturin variants except R63E were expressed in similar amounts resulting in protein concentrations between 1.2-1.7 g/l, and all expressed variants displayed a similar biological activity in vitro compared to wild-type recombinant human neurturin with an $EC_{50}$ between 0.32-0.89 ng/ml (see FIG. 5B). The human recombinant neurturin from *E. coli* used for comparison showed a weaker potency with an $EC_{50}$ of 2.20 ng/ml probably resulting from a portion of not properly refolded neurturin in the sample (see FIG. 5B).

Thus, FIG. 5 shows that modifications in neurturin's "heel" region such as an introduction of a negatively charged, acidic amino acid into the basic patch does not compromise the biological activity of neurturin in general. This is surprising that the prior art shows that a modification from basic to acidic amino acids in the heel region would interfere with the biological activity of neurturin (see sequence and structure comparisons with other GFL, as discussed above).

The failure of expressing neurturin variant R63E shows that at this position a change from arginine to glutamic acid is not tolerated. Nevertheless, other modifications not resulting in a complete change of amino acid charge are functional. A sequence comparison of known neurturin homologs shows that a R63E variant exists in the human neurturin homolog of *Ornithorhynchus anatinus, Monodelphis domestica*, and *Gallus gallus*. Also natural variants of the arginin residues at position 52, 57, 58, and 61 exist in different neurturin homologs (see FIG. 6).

In order to create biologically active neurturin variants with improved bioavailability, the inventors replaced basic arginines in the "heel" region with Lysine. As arginine and lysine are structurally related, such exchanges are expected to affect the structure of the neurturin molecule only minimally. Such changes are enabling the site-specific directed PEGylation of neurturin via the the primary amine of the lysine side chain in a region of the protein shown to tolerate substantial amino acid changes, and which is therefore not important for biological activity. This reaction is highly specific since no lysine is present in the mature native human neurturin sequence. Reactions of activated PEG with other amines are minimized by optimizing reaction conditions, e.g. pH, temperature and reaction time. By placing a PEG modification within the basic patch of the "heel" region, two objectives are achieved: (i) the benefits of protein PEGylation (improved bioavailability via reduced renal clearance, reduced immunogenicity, improved protein stability) can be obtained while minimizing effects on protein activity and (ii) PEGylation in this region is expected to shield the basic patch by preventing interactions with negatively charged cell surface proteoglycans, which is also expected to improve protein bioavailability.

In a first step, the coding sequence of mature human neurturin which is optimized for human codon usage (with an additional N-terminal signal peptide for eukaryotic secretion) and an additional purification tag (repeat of six histidine residues with an additional site for cleavage of this purification tag with factor-Xa) is modified by PCR-based site directed mutagenesis. Here, codons are exchanged at arginine residues 51, 52, 54, 56, 57, 58, 60, 61, 63, or 65 with the codons for lysine residues.

The resulting expression construct referred to as Kr-G3-H6-G3-Xa-rhneurturin in this invention containing the following features:

Kr: DNA-sequence of mouse kringle-containing transmembrane protein 2, amino acids 1-26, signal peptide (GenBank Accession Number NP_082692) for cytoplasmic secretion optimized for human codon usage (amino acid sequence:

MGTPHLQGFLLLFPLLLRLHGASAGS;). SEQ ID NO: 2

GS: DNA-sequence of a glycine spacer optimized for human codon usage (amino acid sequence: GGG).
H6: DNA-sequence of a 6-histidine tag for purification purposes optimized for human codon usage (amino acid sequence: HHHHHH; SEQ ID NO: 3).
Xa: DNA-sequence of Factor-Xa protease recognition site optimized for human codon usage (amino acid sequence: IEGF; SEQ ID NO: 4). Factor-Xa protease cuts C-terminal after the arginine.

rhneurturin: DNA-sequence of mature recombinant human neurturin optimized for human codon usage (amino acid sequence: ARLGARPCGLRELEVRVSELGLGYAS-DETVLFRYCAGACEAAARVYDLGLRRL RQR-RRLRRERVRAQPCCRPTAYEDEVS-FLDAHSRYHTVHELSARECACV; SEQ ID NO: 5). Single arginine codons at positions 51, 52, 54, 56, 57, 58, 60, 61, 63, or 65 are replaced by the lysine codon AAG in the respective neurturin variant expression construct.

The complete DNA sequence of Kr-G3-H6-G3-Xa-rhneurturin (wt) cloned into pMA vector is shown in FIG. 7; SEQ ID NO: 7.

Example 5

Peglyation of Neurturin Variants

The resulting constructs are cloned in the eukaryotic expression vector pcDNA3.1+ which are transfected into HEK-293 cells for the expression of the modified neurturin variants as describe above.

The expressed neurturin variants are purified by ultra-filtration and by affinity chromatography by means of the introduced purification tag.

The structure, purity and biological activity of the resulting neurturin variant preparations are checked by native-PAGE/Western-blot and neurturin activity assay as shown above.

Biological active neurturin variants which are expressed with sufficient yield and are purified to acceptable purity are used for covalent modification with different mono-disperse PEGs. This PEGs have a preferably size of 2.5-30 kDa, are linear or branched and activated with N-hydroxysuccinimide (NHS) ester. The N-hydroxysuccinimide (NHS) ester is spontaneously reactive with primary amines, providing for efficient PEGylation of proteins. Other PEG derivatives are for example but not limited to molecules with different sizes, not mono-disperse or with different branching patterns and coupling chemistries may be applied as well.

After the reaction, the purification tag is cleaved at the introduced proteinase site by factor-Xa and PEG-neurturin variants are purified by size exclusion and/or affinity chromatography.

A number of additional purification tags and protease site/recombinant protease combinations are well known in the art and may replace the His-Tag and/or factor-Xa site/factor Xa cleavage. Alternatively, the neurturin protein containing the introduced PEGylation site(s) may be purified from the supernatant of eukaryotic expression systems or from the lysate or supernatant of overexpressing bacteria without purification tag by chromatographic methods.

The structure, purity and biological activity of the resulting PEG-neurturin variant preparations are checked by SDS-PAGE/Western-blot, native-PAGE/Western-blot, and neurturin activity assay as shown above.

Purified PEG-neurturin variants showing sufficient biological activity in vitro are assayed in vivo for their pharmacokinetic behavior after subcutaneous administration of 50 µmol/kg s.c. to mice and rats. Plasma neurturin concentration is determined by neurturin ELISA at baseline, and at 0.25, 0.5, 1, 1.5, 2, 3, 4, 6 and 8 hours after administration.

Selected PEG-neurturin variants showing improved bioavailability compared to wt neurturin are tested for their efficacy in vivo by subcutaneous administration to neo STZ rats once daily 50 µmol/kg for 6 days. To assay beta-cell function, blood glucose is determined every day, and pancreatic insulin content is determined after 6 days treatment compared to vehicle control and wt neurturin groups.

Example 6

Immunogenic Potential of Pegylated Neurturin

Human recombinant wt neurturin has an immunogenic potential as demonstrated by the appearance of anti-neurturin antibodies after administration to adult mice for more than 2 weeks. The anti-neurturin antibodies have been detected with a specific assay. Briefly, recombinant human neurturin was coated on microplates to capture serum antibodies. After washing, the captured anti-neurturin antibodies were quantified by a luminescence read-out using biotin-conjugated goat anti-IgG antibody or goat anti-IgG/IgM antibody followed by the use of peroxidase conjugated streptavidin. Anti-neurturin IgG and anti-neurturin IgM diluted in serum was used to establish standard curves (see FIG. 8).

As the PEGylation of pharmacologically active proteins reduces their immunogenic potential, selected PEG-neurturin variants with improved bioavailability and sustained potency are tested for their immunogenic potential by subcutaneous administration of once daily 50 µmol/kg for 28 days in adult mice. The appearance of anti-neurturin antibodies is determined by anti-neurturin antibody ELISA every weak compared to vehicle control and wt neurturin groups.

Example 7

Synthesis of a PEGylated Neurturin Variant with an R63K Amino Acid Substitution

A neurturin fusion protein with the structure Kr-$G_3H_6G_3$Xa-rhNTN was designed as a basis for recombinant human neurturin (rhNTN) variants to be secreted from cultured eukaryotic cells, recovered from the cell culture medium supernatant and for subsequent purification and chemical modification with PEG (PEGylation).

The full length human neurturin (amino acid sequence: ARLGARPCGLRELEVRVSELGLGYASDE-TVLFRYCAGACEAAARVYDLGLRRLRQRR RLR-RERVRAQPCCRPTAYEDEVSFLDAH-SRYHTVHELSARECACV, SEQ ID NO: 5) is fused N-terminally to the following components (from N- to C-terminus):

1. Secretion signal peptide consisting of the amino acids 1-26 of the *Mus musculus* kringle-containing transmembrane protein 2 (NP_082692) (Kr; amino acid sequence MGTPHLQGFLLLFPLLLRLHGASAGS, SEQ ID NO:2) for the secretion of the expressed protein into the cell culture medium.
2. Linker made of three glycine residues ($G_3$; amino acid sequence GGG,) for the separation of the signal peptide from the following purification tag.
3. 6-histidine tag for the capture and purification by immobilized metal ion chromatography ($H_6$; amino acid sequence HHHHHH, SEQ ID NO: 3).
4. Linker made of three glycine residues ($G_3$; amino acid sequence GGG,) for the separation of the 6-histidine tag from the following protease site.
5. Recognition site of Factor-Xa protease (Xa; amino acid sequence IEGR, SEQ ID NO: 4) for cleavage at the C-terminus of its arginine leaving neurturin with the natural N-terminus.

The complete coding nucleotide sequence of Kr-$G_3H_6G_3$Xa-rhNTN was synthesized in vitro using an optimized codon usage for higher eukaryotes. The synthesized DNA was ligated into the pcDNA 3.1+ vector (Invitrogen) by means of standard molecular cloning techniques and the integrity of the sequence was controlled by nucleotide sequencing. The coding nucleotide sequence of Kr-$G_3H_6G_3$Xa-rhNTN (SEQ ID NO: 6) is:

```
ATGGGCACCCCACACCTGCAGGGCTTTCTGCTGCTGTTCCCCCTGCTG

CTGCGGCTGCACGGCGCCTCTGCCGGCTCTGGCGGCGGACACCACCA

CCATCACCACGGCGGAGGGATCGAGGGCAGAGCCAGACTGGGCGCCA

GACCCTGCGGCCTGCGGGAGCTGGAAGTGCGGGTGTCCGAGCTGGGC

CTGGGCTACGCCAGCGACGAGACAGTGCTGTTCCGGTACTGCGCTGG

CGCCTGCGAGGCCGCTGCCCGGGTGTACGACCTGGGGCTCCGGAGAC

TGAGACAGCGGCGGAGACTGAGGCGGGAGAGAGTGCGCGCCCAGCCC

TGCTGCAGACCCACCGCCTACGAGGACGAGGTGTCCTTCCTGGACGCC

CACAGCAGATACCACACCGTGCACGAGCTGTCCGCCAGAGAATGCGCC

TGCGTGTGA
```

7.2 Design of a Neurturin Variant R63K Fusion Protein

In order to generate a specific site for the posttranslational chemical attachment of PEG molecules within the basic patch of neurturin, the arginine at amino acid position 63 within the basic patch of rhNTN encoded by AGA was changed by means of PCR mediated mutagenesis to lysine encoded by AAG (R63K). Since the neurturin variant fusion protein only contains a single lysine residue, the primary amino group containing side chain of the introduced lysine will serve as a specific PEGylation site for PEG molecules activated with a carboxylic acid succinimidyl ester group (NHS-PEG). Neurturin is a homo-dimer consisting of two identical amino acid chains. Thus one rhNTN(R63K) protein will now harbor two lysine residues serving as PEGylation sites. The integrity of the sequence was controlled by nucleotide sequencing. The coding nucleotide sequence of Kr-$G_3H_6G_3$Xa-rhNTN (R63K) is (nucleotide exchanges in small letters) (SEQ ID NO: 7):

```
ATGGGCACCCCACACCTGCAGGGCTTTCTGCTGCTGTTCCCCCTGCTG

CTGCGGCTGCACGGCGCCTCTGCCGGCTCTGGCGGCGGACACCACCA

CCATCACCACGGCGGAGGGATCGAGGGCAGAGCCAGACTGGGCGCCA

GACCCTGCGGCCTGCGGGAGCTGGAAGTGCGGGTGTCCGAGCTGGGC

CTGGGCTACGCCAGCGACGAGACAGTGCTGTTCCGGTACTGCGCTGG

CGCCTGCGAGGCCGCTGCCCGGGTGTACGACCTGGGGCTCCGGAGAC

TGAGACAGCGGCGGAGACTGAGGCGGGAGAagGTGCGCGCCCAGCCC

TGCTGCAGACCCACCGCCTACGAGGACGAGGTGTCCTTCCTGGACGCC

CACAGCAGATACCACACCGTGCACGAGCTGTCCGCCAGAGAATGCGCC

TGCGTGTGA
```

7.3 Recombinant Expression of the Neurturin Variant R63K Fusion Protein

The resulting plasmid pcDNA 3.1+ Kr-$G_3H_6G_3$Xa-rhNTN (R63K) was transfected into HEK293 cells by means of PEI-plasmid complexes (Backliwal et al., Biotechnol. Bioeng. 2008 Feb. 15; 99(3):721-7) in order to obtain $G_3H_6G_3$Xa-rhNTN(R63K) protein secreted into the culture medium. The cells were cultured for 4 days in shaker flasks on a horizontal shaker with 70 rpm agitation in Ex-Cell 293 SF medium (Sigma-Aldrich) supplemented with 6 mM L-glutamine (Invitrogen) at 37° C. in a humidified atmosphere containing 5% $CO_2$. The cell culture supernatant was harvested and cleared from cellular contaminations by centrifugation and microfiltration through a 0.2 μm polyethersulfone membrane. The cleared cell culture supernatant was supplemented with 1.5 M NaCl, 20 mM imidazole, 0.1% Tween-20, and 25% glycerol (final concentrations). The pH was adjusted to pH 7.4 with 1 M HCl. $G_3H_6G_3$Xa-rhNTN(R63K) was captured from the supplemented cell culture supernatant on a HisTrap Ni Sepharose Fast Flow column (GE Healthcare) loaded with nickel ions, washed with 50 mM $NaH_2PO_4$, 1.5 M NaCl, 20 mM imidazole, 0.1% Tween-20, 25% glycerol (final concentrations), pH 7.4 and eluted with an increasing imidazole gradient from 20-250 mM in the same buffer. The eluted fractions containing $G_3H_6G_3$Xa-rhNTN(R63K) in the dimeric (MW: 23.6 kDa) or monomeric (MW: 13.3 kDa) form were identified by non reducing SDS-PAGE and Coomassie blue staining (FIG. 9) and pooled. The eluted protein was concentrated by means of ultrafiltration with 10 KDa cut-off until a concentration of 1 pmol/μL was achieved and dialyzed against 30 mM $Na_2B_4O_7$, 150 mM NaCl, pH 9.0.

7.4 PEGylation of the Neurturin Variant R63K Fusion Protein

In order to PEGylate the prepared $G_3H_6G_3$Xa-rhNTN (R63K), NHS-PEG (alpha-methoxy-omega-carboxylic acid succinimidyl ester poly(ethylene glycol)) with a molecular weight of 2 kDa (IRIS Biotech) was added to the protein solution to a final concentration of 30 mM. A control reaction mix without the addition of NHS-PEG was prepared in parallel. The reaction mixes were incubated at 4° C. with 500 rpm agitation for 2 h until termination by addition of glycine to quench residual reactive NHS-moieties. 2.5 mU/μL Factor Xa protease (Novagen) was added to the reaction mixes followed by incubation at 37° C. with 500 rpm agitation for 20 h to cleave off the $G_3H_6G_3$Xa-tag.

The PEGylation and the control reaction mixes were diluted 1:2 with non-reducing Laemmli SDS-PAGE loading buffer. SDS-PAGE and subsequent protein staining with Coomassie blue was performed (FIG. 10). The PEG-free control reaction loaded on lane 2 harbors non-PEGylated rhNTN (R63K) dimer with an apparent MW of 23.4 kDa (a). The PEGylation reaction loaded on lane 3 harbors three fractions: Non-PEGylated rhNTN(R63K) dimer with an apparent MW of 23.4 kDa (a), rhNTN(R63K-PEG) dimer PEGylated at one polypeptide chain with an apparent MW of 25.4 kDa (b), and rhNTN(R63K-$PEG_2$) PEGylated dimer at both polypeptide chains with an apparent MW of 27.4 kDa (c). Thus the protein band c represents the desired di-PEGylated neurturin variant with an additional mass of 4 kDa resulting from the attachment of two 2 kDa PEG moieties. Comparing the relative abundance of the three fractions resulting from the PEGylation reaction shown in lane 3 by measuring the integrated density of the protein bands using ImageJ Software shows that 17% of neurturin is non-PEGylated dimer (a), 28% is mono-PEGylated rhNTN(R63K-PEG) dimer (b) and 55% is the di-PEGylated rhNTN(R63K-$PEG_2$) dimer (c).

As an alternative, the protocol can be changed such that the N-terminal tag is removed from rhNRTN R63K variant protein before the PEGylation reaction, or to perform the PEGylation reaction on untagged rhNTN R63K variant protein purified by means other than Ni-affinity chromatography. This may result in reaction products carrying PEG groups on the introduced lysine as well as on one or both N-terminal amino groups, depending on the reaction conditions.

The invention claimed is:

1. A neurturin conjugate comprising a polyol moiety covalently bound to a human neurturin protein product, wherein said neurturin protein product is capable of dimerizing with a neurturin protein having the amino acid sequence of SEQ ID NO: 5, wherein said neurturin protein product comprises the amino acid sequence of SEQ ID NO: 5 or a biologically active fragment thereof, but with 1, 2, 3, or 4 amino acid alterations, wherein the amino acid alterations are:
   a) the substitution of 1, 2, 3 or 4 arginine residues at amino acid positions 51, 52, 54, 56, 57, 58, 60, 61, 63 or 65 of SEQ ID NO: 5 with a lysine, and/or
   b) the substitution of 1, 2, 3 or 4 arginine residues at amino acid positions 51, 52, 54, 56, 57, 58, 60, 61 or 65 of SEQ ID NO: 5 with a glutamic acid.

2. The neurturin conjugate according to claim 1, wherein the polyol moiety is a polyethylene glycol moiety.

3. The neurturin conjugate according to claim 1, wherein the polyol moiety is a single chain polyol moiety.

4. The neurturin conjugate according to claim 1, wherein the polyol moiety is a branched chain polyol moiety.

5. The neurturin conjugate according to claim 1, wherein the polyol moiety is a polyalkylene glycol moiety.

6. The neurturin conjugate according to claim 1, wherein at least one of the arginine residues 51, 52, 54, 56, 57, 58, 60, 61, 63 or 65 is substituted with a lysine.

7. The neurturin conjugate of claim 6, which consists of two neurturin monomers, and which comprises 1-4 polyol moieties bound to the N-terminus and/or bound to a lysine side chain.

8. The neurturin conjugate of claim 1, wherein the arginine residue 63 is substituted by lysine.

9. The neurturin conjugate of claim 1, wherein the amino acid alterations are the substitution of 1, 2, 3 or 4 arginine residues at amino acid positions 51, 52, 54, 56, 57, 58, 60, 61 or 65 of SEQ ID NO: 5 with a glutamic acid.

10. The neurturin conjugate of claim 1, wherein said neurturin protein product has 1 amino acid alteration.

11. The neurturin conjugate of claim 1, wherein said neurturin protein product has 2 amino acid alterations.

12. The neurturin conjugate of claim 1, wherein said neurturin protein product has 3 amino acid alterations.

13. The neurturin conjugate of claim 1, wherein said neurturin protein product has 4 amino acid alterations.

14. A pharmaceutical composition comprising at least one neurturin protein product conjugated to at least one polyethylene glycol molecule as an active ingredient together with a pharmaceutically acceptable carrier, diluent and/or adjuvant, wherein said neurturin protein product is capable of dimerizing with a neurturin protein having the amino acid sequence of SEQ ID NO: 5, wherein said neurturin protein product comprises the amino acid sequence of SEQ ID NO: 5 or a biologically active fragment thereof, but with 1, 2, 3, or 4 amino acid alterations, wherein the amino acid alterations are:
   a) the substitution of 1, 2, 3 or 4 arginine residues at amino acid positions 51, 52, 54, 56, 57, 58, 60, 61, 63 or 65 of SEQ ID NO: 5 with a lysine, and/or
   b) the substitution of 1, 2, 3 or 4 arginine residues at amino acid positions 51, 52, 54, 56, 57, 58, 60, 61 or 65 of SEQ ID NO: 5 with a glutamic acid.

15. The composition of claim 14, wherein said neurturin protein product is a biologically active fragment of a neurturin protein having the amino acid sequence of SEQ ID NO: 5.

16. The composition of claim 14, wherein said neurturin protein product is mono-PEGylated, comprising a single polyethylene glycol molecule chain.

17. The composition of claim 14, wherein said neurturin protein product is oligo- or poly-PEGylated, comprising two, three, four or several polyethylene glycol molecule chains.

18. The composition of claim 14, wherein said neurturin protein product comprises at least one linear polyethylene glycol molecule chain.

19. The composition of claim 14, wherein said neurturin protein product comprises at least one branched polyethylene glycol molecule chain.

20. The composition of claim 14, wherein said polyethylene glycol molecule has an average molecular weight of 100 to 10000 Da.

21. The composition of claim 14, wherein said polyethylene glycol molecule is linked to the N-terminal amino acid of said neurturin protein product.

22. The composition of claim 14, wherein said polyethylene glycol molecule is linked to said neurturin protein product via an acyl or alkyl linkage.

23. The composition of claim 14, wherein said polyethylene glycol molecule is terminated by an OH—, $OCH_3$— or OEt-group.

24. The composition of claim 14, which has an increased bioavailability of the active ingredient compared to a composition with an unmodified control neurturin protein product.

25. The composition of claim 14 for injection or infusion.

26. The composition of claim 25 for subcutaneous or intravenous injection.

27. The composition of claim 14 for administration to a mammal.

28. The pharmaceutical composition of claim 14, wherein said neurturin protein product has 1 amino acid alteration.

29. The pharmaceutical composition of claim 14, wherein said neurturin protein product has 2 amino acid alterations.

30. The pharmaceutical composition of claim 14, wherein said neurturin protein product has 3 amino acid alterations.

31. The pharmaceutical composition of claim 14, wherein said neurturin protein product has 4 amino acid alterations.

32. A variant of human neurturin comprising a human neurturin protein product, wherein said human neurturin protein product is capable of dimerizing with a neurturin protein having the amino acid sequence of SEQ ID NO: 5, wherein said human neurturin protein product comprises the amino acid sequence of SEQ ID NO: 5 or a biologically active fragment thereof, but with 1, 2, 3, or 4 amino acid alterations, wherein the amino acid alterations are:
   a) the substitution of 1, 2, 3 or 4 arginine residues at amino acid positions 51, 52, 54, 56, 57, 58, 60, 61, 63 or 65 of SEQ ID NO: 5 with a lysine, and/or
   b) the substitution of 1, 2, 3 or 4 arginine residues at amino acid positions 51, 52, 54, 56, 57, 58, 60, 61 or 65 of SEQ ID NO: 5 with a glutamic acid.

33. The variant of human neurturin according to claim 32, wherein the arginine residue at position 63 is substituted by lysine.

34. The variant of human neurturin according to claim 32, wherein at least one arginine residue at amino acid position 51, 52, 54, 56, 57, 58, 60, 61 or 65 is substituted by glutamic acid.

35. The variant of human neurturin according to claim 32, wherein the amino acid alterations are the substitution of 1, 2, 3 or 4 arginine residues at amino acid positions 51, 52, 54, 56, 57, 58, 60, 61, 63 or 65 of SEQ ID NO: 5 with a lysine.

36. The human neurturin variant of claim 32, wherein said neurturin protein product has 1 amino acid alteration.

37. The human neurturin variant of claim 32, wherein said neurturin protein product has 2 amino acid alterations.

38. The human neurturin variant of claim 32, wherein said neurturin protein product has 3 amino acid alterations.

39. The human neurturin variant of claim 32, wherein said neurturin protein product has 4 amino acid alterations.

* * * * *

SEQUENCE LISTING

<160> NUMBER OF SEQ ID NOS: 19

<210> SEQ ID NO 1
<211> LENGTH: 197
<212> TYPE: PRT
<213> ORGANISM: Homo sapiens

<400> SEQUENCE: 1

Met Gln Arg Trp Lys Ala Ala Ala Leu Ala Ser Val Leu Cys Ser Ser
1               5                   10                  15

Val Leu Ser Ile Trp Met Cys Arg Glu Gly Leu Leu Ser His Arg
            20                  25                  30

Leu Gly Pro Ala Leu Val Pro Leu His Arg Leu Pro Arg Thr Leu Asp
        35                  40                  45

Ala Arg Ile Ala Arg Leu Ala Gln Tyr Arg Ala Leu Leu Gln Gly Ala
    50                  55                  60

Pro Asp Ala Met Glu Leu Arg Glu Leu Thr Pro Trp Ala Gly Arg Pro
65                  70                  75                  80

Pro Gly Pro Arg Arg Ala Gly Pro Arg Arg Arg Ala Arg Ala
                85                  90                  95

Arg Leu Gly Ala Arg Pro Cys Gly Leu Arg Glu Leu Glu Val Arg Val
                100                 105                 110

Ser Glu Leu Gly Leu Gly Tyr Ala Ser Asp Glu Thr Val Leu Phe Arg
                115                 120                 125

Tyr Cys Ala Gly Ala Cys Glu Ala Ala Ala Arg Val Tyr Asp Leu Gly
            130                 135                 140

Leu Arg Arg Leu Arg Gln Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
                180                 185                 190

Glu Cys Ala Cys Val
        195

<210> SEQ ID NO 2
<211> LENGTH: 26
<212> TYPE: PRT
<213> ORGANISM: Mus musculus

<400> SEQUENCE: 2

Met Gly Thr Pro His Leu Gln Gly Phe Leu Leu Leu Phe Pro Leu Leu
1               5                   10                  15

Leu Arg Leu His Gly Ala Ser Ala Gly Ser
            20                  25

<210> SEQ ID NO 3
<211> LENGTH: 6
<212> TYPE: PRT
<213> ORGANISM: Artificial Sequence
<220> FEATURE:
<223> OTHER INFORMATION: 6 - Histidine Tag

<400> SEQUENCE: 3

His His His His His His
1               5

<210> SEQ ID NO 4
<211> LENGTH: 4

```
<212> TYPE: PRT
<213> ORGANISM: Artificial Sequence
<220> FEATURE:
<223> OTHER INFORMATION: Factor Xa protease recognition site

<400> SEQUENCE: 4

Ile Glu Gly Arg
1

<210> SEQ ID NO 5
<211> LENGTH: 102
<212> TYPE: PRT
<213> ORGANISM: Artificial Sequence
<220> FEATURE:
<223> OTHER INFORMATION: mature recombinant human neurturin

<400> SEQUENCE: 5

Ala Arg Leu Gly Ala Arg Pro Cys Gly Leu Arg Glu Leu Glu Val Arg
1               5                   10                  15

Val Ser Glu Leu Gly Leu Gly Tyr Ala Ser Asp Glu Thr Val Leu Phe
            20                  25                  30

Arg Tyr Cys Ala Gly Ala Cys Glu Ala Ala Ala Arg Val Tyr Asp Leu
        35                  40                  45

Gly Leu Arg Arg Leu Arg Gln Arg Arg Arg Leu Arg Arg Glu Arg Val
    50                  55                  60

Arg Ala Gln Pro Cys Cys Arg Pro Thr Ala Tyr Glu Asp Glu Val Ser
65                  70                  75                  80

Phe Leu Asp Ala His Ser Arg Tyr His Thr Val His Glu Leu Ser Ala
                85                  90                  95

Arg Glu Cys Ala Cys Val
            100

<210> SEQ ID NO 6
<211> LENGTH: 438
<212> TYPE: DNA
<213> ORGANISM: Artificial Sequence
<220> FEATURE:
<223> OTHER INFORMATION: coding nucleotide sequence of Kr-G3H6G3Xa-rhNTN

<400> SEQUENCE: 6
atgggcaccc cacacctgca gggctttctg ctgctgttcc ccctgctgct gcggctgcac      60
ggcgcctctg ccggctctgg cggcggacac caccaccatc accacggcgg agggatcgag     120
ggcagagcca gactgggcgc cagaccctgc ggcctgcggg agctggaagt gcgggtgtcc     180
gagctgggcc tgggctacgc cagcgacgag acagtgctgt tccggtactg cgctggcgcc     240
tgcgaggccg ctgcccgggt gtacgacctg ggcctccgga gactgagaca gcggcggaga     300
ctgaggcggg agagagtgcg cgcccagccc tgctgcagac ccaccgccta cgaggacgag     360
gtgtccttcc tggacgccca cagcagatac acaccgtgc acgagctgtc cgccagagaa     420
tgcgcctgcg tgtgatga                                                   438

<210> SEQ ID NO 7
<211> LENGTH: 435
<212> TYPE: DNA
<213> ORGANISM: Artificial Sequence
<220> FEATURE:
<223> OTHER INFORMATION: Coding nucleotide sequence of Kr-G3H6G3Xa-rhNTN
      (R63K)

<400> SEQUENCE: 7
atgggcaccc cacacctgca gggctttctg ctgctgttcc ccctgctgct gcggctgcac      60
```

-continued

```
ggcgcctctg ccggctctgg cggcggacac caccaccatc accacggcgg agggatcgag      120
ggcagagcca gactgggcgc cagaccctgc ggcctgcggg agctggaagt gcgggtgtcc      180
gagctgggcc tgggctacgc cagcgacgag acagtgctgt tccggtactg cgctggcgcc      240
tgcgaggccg ctgcccgggt gtacgacctg gggctccgga gactgagaca gcggcggaga      300
ctgaggcggg agagagtgcg cgcccagccc tgctgcagac ccaccgccta cgaggacgag      360
gtgtccttcc tggacgccca cagcagatac cacaccgtgc acgagctgtc cgccagagaa      420
tgcgcctgcg tgtga                                                       435
```

<210> SEQ ID NO 8
<211> LENGTH: 23
<212> TYPE: PRT
<213> ORGANISM: Homo sapiens

<400> SEQUENCE: 8

Asp Leu Gly Leu Arg Arg Leu Arg Gln Arg Arg Arg Leu Arg Arg Glu
1               5                   10                  15

Arg Val Arg Ala Gln Pro Cys
            20

<210> SEQ ID NO 9
<211> LENGTH: 23
<212> TYPE: PRT
<213> ORGANISM: Macaca mulatta

<400> SEQUENCE: 9

Asp Leu Gly Leu Arg Arg Leu Arg Gln Arg Arg Arg Leu Arg Arg Glu
1               5                   10                  15

Arg Val Arg Ala Gln Pro Cys
            20

<210> SEQ ID NO 10
<211> LENGTH: 23
<212> TYPE: PRT
<213> ORGANISM: Bos taurus

<400> SEQUENCE: 10

Asp Leu Gly Leu Arg Arg Leu Arg Gln Arg Arg Arg Val Arg Arg Glu
1               5                   10                  15

Arg Val Arg Ala Gln Pro Cys
            20

<210> SEQ ID NO 11
<211> LENGTH: 23
<212> TYPE: PRT
<213> ORGANISM: Canis familiaris

<400> SEQUENCE: 11

Asp Leu Gly Leu Arg Arg Leu Arg Gln Arg Arg Arg Val Arg Arg Glu
1               5                   10                  15

Arg Val Arg Ala Gln Pro Cys
            20

<210> SEQ ID NO 12
<211> LENGTH: 23
<212> TYPE: PRT
<213> ORGANISM: Mus musculus

<400> SEQUENCE: 12

Asp Leu Gly Leu Arg Arg Leu Arg Gln Arg Arg Val Arg Arg Glu
1               5                   10                  15

Arg Ala Arg Ala His Pro Cys
            20

<210> SEQ ID NO 13
<211> LENGTH: 23
<212> TYPE: PRT
<213> ORGANISM: Rattus norvegicus

<400> SEQUENCE: 13

Asp Leu Gly Leu Arg Arg Leu Arg Gln Arg Arg Val Arg Lys Glu
1               5                   10                  15

Arg Val Arg Ala His Pro Cys
            20

<210> SEQ ID NO 14
<211> LENGTH: 23
<212> TYPE: PRT
<213> ORGANISM: Ornithorhynchus anatinus

<400> SEQUENCE: 14

Asp Leu Gly Leu Arg Arg Leu Arg Gln Arg Arg Val Arg Lys Glu
1               5                   10                  15

Lys Val Arg Ala Gln Pro Cys
            20

<210> SEQ ID NO 15
<211> LENGTH: 23
<212> TYPE: PRT
<213> ORGANISM: Monodelphis domestica

<400> SEQUENCE: 15

Asp Leu Gly Leu Arg Arg Leu Arg Gln Arg Arg Val Arg Lys Glu
1               5                   10                  15

Lys Ile Arg Ala Arg Pro Cys
            20

<210> SEQ ID NO 16
<211> LENGTH: 23
<212> TYPE: PRT
<213> ORGANISM: Gallus gallus

<400> SEQUENCE: 16

Asp Leu Ser Leu Lys Ser Val Arg Ser Arg Lys Lys Ile Arg Lys Glu
1               5                   10                  15

Lys Val Arg Ala Arg Pro Cys
            20

<210> SEQ ID NO 17
<211> LENGTH: 531
<212> TYPE: DNA
<213> ORGANISM: Artificial Sequence
<220> FEATURE:
<223> OTHER INFORMATION: pMA vector + KrG3H6G3Xa-rhneurturin - Forward
      Strand

<400> SEQUENCE: 17
gagcggaagg cccatgaggc cagttaatta agaggtacca agcttgccac catgggcacc      60
ccacacctgc agggctttct gctgctgttc cccctgctgc tgcggctgca cggcgcctct     120
gccggctctg gcggcggaca ccaccaccat caccacggcg agggatcga gggcagagcc     180

-continued

```
agactgggcg ccagaccctg cggcctgcgg gagctggaag tgcgggtgtc cgagctgggc    240
ctgggctacg ccagcgacga gacagtgctg ttccggtact gcgctggcgc ctgcgaggcc    300
gctgcccggg tgtacgacct ggggctccgg agactgagac agcggcggag actgaggcgg    360
gagagagtgc gcgcccagcc ctgctgcaga cccaccgcct acgaggacga ggtgtccttc    420
ctggacgccc acagcagata ccacaccgtg cacgagctgt ccgccagaga atgcgcctgc    480
gtgtgatgac tcgagctcat ggcgcgccta ggccttgacg gccttccgcc a             531
```

```
<210> SEQ ID NO 18
<211> LENGTH: 531
<212> TYPE: DNA
<213> ORGANISM: Artificial Sequence
<220> FEATURE:
<223> OTHER INFORMATION: pMA vector + KrG3H6G3Xa-rhneurturin - Reverse
      Complement

<400> SEQUENCE: 18
```

```
tggcggaagg ccgtcaaggc ctaggcgcgc catgagctcg agtcatcaca cgcaggcgca    60
ttctctggcg gacagctcgt gcacggtgtg gtatctgctg tgggcgtcca ggaaggacac   120
ctcgtcctcg taggcggtgg gtctgcagca gggctgggcg cgcactctct cccgcctcag   180
tctccgccgc tgtctcagtc tccggagccc caggtcgtac acccgggcag cggcctcgca   240
ggcgccagcg cagtaccgga acagcactgt ctcgtcgctg gcgtagccca ggcccagctc   300
ggacacccgc acttccagct cccgcaggcc gcagggtctg gcgcccagtc tggctctgcc   360
ctcgatccct ccgccgtggt gatggtggtg gtgtccgccg ccagagccgg cagaggcgcc   420
gtgcagccgc agcagcaggg ggaacagcag cagaaagccc tgcaggtgtg gggtgcccat   480
ggtggcaagc ttggtacctc ttaattaact ggcctcatgg gccttccgct c             531
```

```
<210> SEQ ID NO 19
<211> LENGTH: 144
<212> TYPE: PRT
<213> ORGANISM: Artificial Sequence
<220> FEATURE:
<223> OTHER INFORMATION: Kr-G3H6G3Xa-rhNTN - fusion protein

<400> SEQUENCE: 19
```

```
Met Gly Thr Pro His Leu Gln Gly Phe Leu Leu Leu Phe Pro Leu Leu
1               5                   10                  15

Leu Arg Leu His Gly Ala Ser Ala Ser Gly Gly Gly His His
            20                  25                  30

His His His Gly Gly Gly Ile Glu Gly Arg Ala Arg Leu Gly Ala Arg
            35                  40                  45

Pro Cys Gly Leu Arg Glu Leu Glu Val Arg Val Ser Glu Leu Gly Leu
50                  55                  60

Gly Tyr Ala Ser Asp Glu Thr Val Leu Phe Arg Tyr Cys Ala Gly Ala
65                  70                  75                  80

Cys Glu Ala Ala Ala Arg Val Tyr Asp Leu Gly Leu Arg Arg Leu Arg
                85                  90                  95

Gln Arg Arg Arg Leu Arg Arg Glu Arg Val Arg Ala Gln Pro Cys Cys
            100                 105                 110

Arg Pro Thr Ala Tyr Glu Asp Glu Val Ser Phe Leu Asp Ala His Ser
        115                 120                 125

Arg Tyr His Thr Val His Glu Leu Ser Ala Arg Glu Cys Ala Cys Val
    130                 135                 140
```